(12) United States Patent
Melker

(10) Patent No.: US 6,981,947 B2
(45) Date of Patent: Jan. 3, 2006

(54) METHOD AND APPARATUS FOR MONITORING RESPIRATORY GASES DURING ANESTHESIA

(75) Inventor: Richard J. Melker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 69 days.

(21) Appl. No.: 10/178,877

(22) Filed: Jun. 24, 2002

(65) Prior Publication Data

US 2003/0176804 A1 Sep. 18, 2003

Related U.S. Application Data

(63) Continuation-in-part of application No. 10/054,619, filed on Jan. 22, 2002.

(51) Int. Cl.
  *A61B 5/08* (2006.01)
(52) U.S. Cl. ........................... 600/532; 600/529
(58) Field of Classification Search ................ 600/532, 600/531, 529, 538, 533; 128/203.12, 203.13, 128/203.14, 203.15, 203.18, 203.22, 203.25, 128/204.18, 204.22, 204.23; 73/23.3
See application file for complete search history.

(56) References Cited

U.S. PATENT DOCUMENTS

| | | |
|---|---|---|
| 3,567,029 A | 3/1971 | Quame |
| 3,608,546 A | 9/1971 | Shinn |
| 3,649,199 A | 3/1972 | Littlejohn |
| 3,792,272 A | 2/1974 | Harte et al. |
| 3,877,291 A | 4/1975 | Hoppesch et al. |
| 3,951,607 A | 4/1976 | Fraser |
| 3,955,926 A | 5/1976 | Fischer |
| 4,150,670 A | 4/1979 | Jewett et al. |
| 4,202,352 A | 5/1980 | Osborn |
| 4,215,409 A * | 7/1980 | Strowe ...................... 700/285 |
| 4,312,228 A | 1/1982 | Wohltjen |
| 4,314,564 A | 2/1982 | Albarda |
| 4,334,540 A | 6/1982 | Preti et al. |
| 4,346,584 A | 8/1982 | Boehringer |
| 4,349,626 A | 9/1982 | Labows et al. |
| 4,361,026 A | 11/1982 | Muller et al. |
| 4,399,686 A | 8/1983 | Kindlund et al. |
| 4,432,226 A | 2/1984 | Dempster |
| 4,456,014 A | 6/1984 | Buck et al. |
| 4,534,360 A | 8/1985 | Williams |
| 4,734,777 A | 3/1988 | Okino et al. |

(Continued)

FOREIGN PATENT DOCUMENTS

DE  19607646 A1  9/1997

(Continued)

OTHER PUBLICATIONS

Parry AD et al. (1995) "Leg ulcer odour detection identified beta-haemolytic streptococcal infection," *Journal of Wound Care*, 4:404-406.

(Continued)

*Primary Examiner*—Max F. Hindenburg
*Assistant Examiner*—Navin Natnithithadha
(74) *Attorney, Agent, or Firm*—Saliwanchik, Lloyd & Saliwanchik

(57) ABSTRACT

A method and system is provided for monitoring delivery of anesthesia (inhalational and intravenous) and detecting the depth of anesthesia wherein at least one anesthetic agent is absorbed in patient's bloodstream during the administration of anesthesia, which includes sampling inspired and expired gas; analyzing the gas for concentration of at least one substance indicative of the anesthetic agent using sensor technology such as free (unmetabolized) anesthetic agent or its metabolites; determining the effect of the agent based on that concentration; and determining depth of anesthesia based thereon.

36 Claims, 10 Drawing Sheets

U.S. PATENT DOCUMENTS

| | | | |
|---|---|---|---|
| 4,735,777 A | 4/1988 | Mitsui et al. | |
| 4,772,559 A | 9/1988 | Preti et al. | |
| 4,796,639 A | 1/1989 | Snow et al. | |
| 4,868,545 A | 9/1989 | Jones | |
| 4,895,017 A | 1/1990 | Pyke et al. | |
| 4,938,928 A | 7/1990 | Koda et al. | |
| 4,992,244 A | 2/1991 | Grate | |
| 5,003,985 A | 4/1991 | White et al. | |
| 5,034,192 A | 7/1991 | Wrighton et al. | |
| 5,042,501 A | 8/1991 | Kenny et al. | |
| 5,060,506 A | 10/1991 | Douglas | |
| 5,071,770 A | 12/1991 | Kolesar, Jr. | |
| 5,081,871 A | 1/1992 | Glaser | |
| 5,082,630 A | 1/1992 | Partin et al. | |
| 5,094,235 A * | 3/1992 | Westenskow et al. | 128/204.22 |
| 5,111,827 A | 5/1992 | Rantala | |
| 5,137,692 A | 8/1992 | Fritz | |
| 5,145,645 A | 9/1992 | Zakin et al. | |
| 5,167,972 A | 12/1992 | Greenberg et al. | |
| 5,179,027 A | 1/1993 | Fisher | |
| 5,252,292 A | 10/1993 | Hirata et al. | |
| 5,296,706 A * | 3/1994 | Braig et al. | 250/339.13 |
| 5,303,575 A | 4/1994 | Brown et al. | |
| 5,317,156 A | 5/1994 | Cooper et al. | |
| 5,325,704 A | 7/1994 | Mariani et al. | |
| 5,351,522 A | 10/1994 | Lura | |
| 5,361,771 A | 11/1994 | Craine et al. | |
| 5,409,839 A | 4/1995 | Balestrieri et al. | |
| 5,425,374 A | 6/1995 | Ueda et al. | |
| 5,447,165 A | 9/1995 | Gustafsson | |
| 5,453,359 A | 9/1995 | Gargan et al. | |
| 5,465,608 A | 11/1995 | Lokshin et al. | |
| 5,466,700 A | 11/1995 | Batenhorst et al. | |
| 5,482,601 A | 1/1996 | Ohshima et al. | |
| 5,495,744 A * | 3/1996 | Ueda et al. | 73/1.07 |
| 5,501,212 A | 3/1996 | Psaros | |
| 5,528,924 A | 6/1996 | Wajid et al. | |
| 5,547,878 A | 8/1996 | Kell | |
| 5,558,083 A | 9/1996 | Bathe et al. | |
| 5,560,352 A | 10/1996 | Heim et al. | |
| 5,571,401 A | 11/1996 | Lewis et al. | |
| 5,573,005 A | 11/1996 | Ueda et al. | |
| 5,573,955 A | 11/1996 | Khanna et al. | |
| 5,605,612 A | 2/1997 | Park et al. | |
| 5,634,517 A | 6/1997 | Linden et al. | |
| 5,645,072 A | 7/1997 | Thrall et al. | |
| 5,716,852 A | 2/1998 | Yager et al. | |
| 5,756,879 A | 5/1998 | Yamagishi et al. | |
| 5,771,890 A | 6/1998 | Tamada | |
| 5,776,783 A | 7/1998 | Kell | |
| 5,783,154 A | 7/1998 | Althainz et al. | |
| 5,783,449 A | 7/1998 | Kuznetsov | |
| 5,795,787 A | 8/1998 | Silkoff et al. | |
| 5,801,297 A | 9/1998 | Mifsud et al. | |
| 5,826,577 A | 10/1998 | Perroz et al. | |
| 5,830,412 A | 11/1998 | Kimura et al. | |
| 5,861,254 A | 1/1999 | Schneider et al. | |
| 5,866,434 A | 2/1999 | Massey et al. | |
| 5,891,398 A | 4/1999 | Lewis et al. | |
| 5,900,552 A | 5/1999 | Chu et al. | |
| 5,918,257 A | 6/1999 | Mifsud et al. | |
| 5,925,014 A * | 7/1999 | Teeple Jr. | 358/1.15 |
| 5,928,167 A | 7/1999 | Wagner et al. | |
| 5,932,877 A | 8/1999 | Braig et al. | |
| 5,945,069 A | 8/1999 | Buehler | |
| 5,950,630 A | 9/1999 | Portwood et al. | |
| 5,954,685 A | 9/1999 | Tierney | |
| 5,958,896 A | 9/1999 | Renshaw et al. | |
| 5,962,335 A | 10/1999 | Katzman | |
| 5,971,937 A | 10/1999 | Ekström | |
| 5,996,586 A | 12/1999 | Phillips | |
| 6,007,775 A | 12/1999 | Yager | |
| 6,010,459 A | 1/2000 | Silkoff et al. | |
| 6,025,200 A | 2/2000 | Kaish et al. | |
| 6,057,162 A | 5/2000 | Rounbehler et al. | |
| 6,063,243 A | 5/2000 | Zettl et al. | |
| 6,067,167 A | 5/2000 | Atkinson et al. | |
| 6,074,345 A | 6/2000 | van Oostrom et al. | |
| 6,085,576 A | 7/2000 | Sunshine et al. | |
| 6,094,681 A | 7/2000 | Shaffer et al. | |
| 6,097,485 A | 8/2000 | Lievan | |
| 6,120,443 A * | 9/2000 | Cohen-Laroque | 600/300 |
| 6,131,571 A * | 10/2000 | Lampotang et al. | 128/204.21 |
| 6,136,801 A | 10/2000 | Kell | |
| 6,153,147 A | 11/2000 | Craig | |
| 6,180,414 B1 | 1/2001 | Katzman | |
| 6,186,977 B1 * | 2/2001 | Andrews et al. | 604/67 |
| 6,190,858 B1 | 2/2001 | Persaud et al. | |
| 6,203,814 B1 | 3/2001 | Fisher et al. | |
| 6,216,690 B1 | 4/2001 | Keitel et al. | |
| 6,221,026 B1 | 4/2001 | Phillips | |
| 6,234,006 B1 | 5/2001 | Sunshine et al. | |
| 6,237,397 B1 | 5/2001 | Shinar et al. | |
| 6,244,096 B1 | 6/2001 | Lewis et al. | |
| 6,248,078 B1 | 6/2001 | Risby et al. | |
| 6,251,082 B1 | 6/2001 | Rayburn | |
| 6,261,783 B1 | 7/2001 | Jayasena et al. | |
| 6,264,913 B1 | 7/2001 | Wagner | |
| 6,277,081 B1 * | 8/2001 | Susi et al. | 600/532 |
| 6,283,953 B1 | 9/2001 | Ayer et al. | |
| 6,303,316 B1 | 10/2001 | Kiel et al. | |
| 6,305,212 B1 | 10/2001 | Drzewiecki | |
| 6,312,390 B1 | 11/2001 | Phillips | |
| 6,319,724 B1 | 11/2001 | Lewis et al. | |
| 6,328,708 B1 | 12/2001 | Georgieff | |
| 6,341,520 B1 | 1/2002 | Satoh et al. | |
| 6,363,772 B1 | 4/2002 | Berry | |
| 6,387,329 B1 | 5/2002 | Lewis et al. | |
| 6,399,302 B1 | 6/2002 | Lannigan et al. | |
| 6,416,479 B1 | 7/2002 | Seidman | |
| 6,455,319 B1 | 9/2002 | Lewis et al. | |
| 6,467,333 B2 | 10/2002 | Lewis et al. | |
| 6,479,019 B1 | 11/2002 | Goldstein et al. | |
| 6,495,824 B1 | 12/2002 | Atkinson | |
| 6,511,453 B2 | 1/2003 | Georgieff | |
| 6,558,626 B1 | 5/2003 | Aker et al. | |
| 6,589,727 B1 | 7/2003 | Klenerman et al. | |
| 6,597,438 B1 | 7/2003 | Cabuz et al. | |
| 6,598,459 B1 | 7/2003 | Fu | |
| 6,599,253 B1 | 7/2003 | Baum et al. | |
| 6,599,281 B1 | 7/2003 | Struys et al. | |
| 6,620,800 B1 | 9/2003 | Roberts, II | |
| 6,631,333 B1 | 10/2003 | Lewis et al. | |
| 6,727,075 B2 | 4/2004 | Fitzgerald et al. | |
| 6,755,783 B2 | 6/2004 | Cosentino et al. | |
| 2001/0021815 A1 | 9/2001 | Katzman et al. | |
| 2001/0041366 A1 | 11/2001 | Lewis et al. | |
| 2001/0046674 A1 | 11/2001 | Ellington | |
| 2001/0050228 A1 | 12/2001 | Jaeger | |
| 2001/0055544 A1 | 12/2001 | Copp | |
| 2002/0007249 A1 | 1/2002 | Cranley et al. | |
| 2002/0007687 A1 | 1/2002 | Zimmermann et al. | |
| 2002/0014236 A1 | 2/2002 | Dittmann et al. | |
| 2002/0017300 A1 | 2/2002 | Hickle et al. | |
| 2002/0034757 A1 | 3/2002 | Cubicciotti | |
| 2002/0068295 A1 | 6/2002 | Madou et al. | |
| 2002/0173729 A1 | 11/2002 | Viertio-Oja et al. | |
| 2003/0004426 A1 | 1/2003 | Melker et al. | |
| 2003/0008407 A1 | 1/2003 | Fu | |
| 2003/0059820 A1 | 3/2003 | Vo-Dinh | |
| 2003/0087239 A1 | 5/2003 | Stanton et al. | |
| 2003/0119065 A1 | 6/2003 | Lin et al. | |
| 2003/0139681 A1 | 7/2003 | Melker et al. | |
| 2003/0216660 A1 | 11/2003 | Ben-Oren et al. | |

| | | |
|---|---|---|
| 2004/0027246 A1 | 2/2004 | Aguglia |
| 2004/0101477 A1 | 5/2004 | Leyland-Jones |
| 2005/0065446 A1 | 3/2005 | Talton |

FOREIGN PATENT DOCUMENTS

| | | |
|---|---|---|
| DE | 29902593 | 8/1999 |
| EP | 0 370 151 A1 | 5/1990 |
| EP | 0 979 977 A1 | 2/2000 |
| GB | 829409 A | 3/1960 |
| GB | 2 309 166 A | 7/1997 |
| GB | 2 329 245 A | 3/1999 |
| JP | 08313407 A | 11/1996 |
| JP | 09196915 A | 7/1997 |
| RU | 2104535 C1 | 2/1998 |
| WO | WO 92/10749 | 6/1992 |
| WO | WO 95/08113 A1 | 3/1995 |
| WO | WO 95/31718 | 11/1995 |
| WO | WO 87/02773 A1 | 2/1998 |
| WO | WO 98/57145 A1 | 12/1998 |
| WO | WO 99/12471 | 3/1999 |
| WO | WO 99/66304 | 12/1999 |
| WO | WO 00/25108 A1 | 5/2000 |
| WO | WO 00/67820 | 11/2000 |
| WO | WO 00/79243 A1 | 12/2000 |
| WO | WO 01/34024 | 5/2001 |
| WO | WO 01/93743 | 12/2001 |
| WO | WO 2002/079514 A1 | 10/2002 |
| WO | WO 03/016901 A1 | 2/2003 |
| WO | WO 03/045473 | 6/2003 |
| WO | WO 2004/065404 A1 | 8/2004 |

OTHER PUBLICATIONS

Huang, J.W. et. al. (Aug. 1, 1996) "Depth of anesthesia estimating & propofol delivery system," http://www.rpi.edu/~royr/roy_descpyt.html.

Kenny, G. "Target-controlled infusions-pharmacokinetic and pharmacodynamic variations," http://www.anaesthesiologie.med.uni-erlangen.de/esctaic97/a_kenny.htm.

Chandiok S, et al. (1997) Screening for bacterial vaginosis: a novel application of artificial nose technology, *Journal of Clinical Pathology*, 50/(9):790-791.

Hanson, III, CW, Steinberger HA (Sep. 1997) "The use of a novel electronic nose to diagnose the presence of intrapulmonary infection," *Anesthesiology*, 87 (3A), Abstract A269.

Groves, W.A. et al. (1998) "Analyzing organic vapors in exhaled breath using a surface acoustic wave sensor array with preconcentration: Selection and characterization of the preconcentrator adsorbent, "*Analytica Chimica Acta* pp. 131-143.

Kuipers, J.A. et al. (1999) "Fast-pass lung uptake and pulmonary clearance of propofol," *Anesthesiology* 91:1780-1787.

Fujita, A. et al. (2000) "A Simple method for detecting plasma propofol," *Anesth. Analog* 90:1452-1454.

Fang, M. et al., "Detection of Organic Chemicals by SAW Sensor Array," *Sensors and Actuators*, 1999, vol. B56, pp. 155-157.

Frauendorf C. et al., "Detection of Small Organic Analytes by Fluorescing Molecular Switches" *Bioorganic & Medicinal Chemistry 9*, 2001, pp. 2521-2524.

Jayasena S., "Aptamers: An Emerging Class of Molecules That Rival Antibodies in Diagnostics" *Clinical Chemistry*, 1999, vol. 45, No. 9, pp. 1628-1650.

Phillips, M., "Breath Tests in Medicine" *Scientific American*, 1992, pp. 52-57, XP001080159.

Stojanovic M. et al., "Aptamer-Based Folding Fluorescent Sensor for Cocaine" *Journal of the American Chemistry Society*, 2001, vol. 123, pp. 4928-4931.

Wohltjen, H. et al., "Determination of Partition Coefficients from Surface Acoustic Wave Vapor Senor Responses and Correlation with Gas—Liquid Chromatographic Partition Coefficients", *Anal. Chem.* (1988), 60: 869-875.

Wohltjen, H. et al., "Surface Acoustic Wave Devices for Chemical Analysis", *Anal. Chem.* (1989), pp. 704A-712A, vol. 61, No. 11.

Wohltjen, H. et al., "Vapor Detection with Surface Acoustic Wave Microsensors", *Chemical Sensors and Microinstrumentation* (1989), pp. 157-175.

Dickinson, T. A. et al., "Current Trends in 'Artificial-Nose'Technology," *Tib Tech,* 1998, 16:250-258.

Fisher et al., "A man-portable chemical sniffer utilizing Novel Fluorescent polymers for detection of ultra-trace concentrations of explosives emanating from landmines," *Nomadics Inc.* (2000), pp. 1-10.

Ganga-Zandzou, P.S. et al., "A 13C-urea breath test in children with *Helicobacter pylori* infection: validity of the use of a mask to collect exhaled breath sample," *Acta. Paediatr.* (2001), vol. 90, pp. 232-233.

Hammon III, W. S. et al., "Forensic GPR: Finite-Difference Simulations of Responses From Buried Human Remains," *Journal of Applied Geophysics,* (2000), 45:171-186.

Hong, C. et al., "Carbon Nanotube-Enhanced Electrochemical DNA Biosensor for DNA Hybridization Detection" (2003), *Anal. Bioanal. Chem.,* 375:287-293.

Liebich et al., "Volatile Substances in Blood Serum: a Profile Analysis and Quantitative Determination," *Journal of Chromatography* (1977), vol. 142, pp. 505-516.

Miller III, E. R. et al., "Association Between Cigarette Smoking and Lipid Peroxidation in a Controlled Feeding Study," *Circulation,* (1997), vol. 142, pp. 96(4):1097-1101.

Mueller et al. "Experience in mass spectrometric identification in acute poisoning," *Beitr. Diagn. Ther, Akuter. Intox., Vortr. Symp. 4th* (1982), pp. 126-134, Abstract Only.

Pantarotto D. et al., "Synthesis, Structural Characterization, and Immunological Properties of Carbon Nanotubes Functionalized with Peptides" (2003), *J. Am. Chem. Soc.,* 125:6160-6164.

Pavlou and Turner. "Sniffing out the truth: Clinical Diagnosis Using the Electronic Nose," *Clin. Chem. Lab. Med.* (2000), vol. 38, number 2, pp. 99-112.

Perri, F. "Diagnosis of *Helicobacter pylori* infection: which is best? The urea breath test, " *Dig. Liver. Dis.* (2000), vol. 32, Supp. 3, pp. S196-198.

Pilar Kraman, "Prescription Drug Diversion," *Trends Alert* provided by the Council of State Government at www.csg.org (Apr. 2004).

Rogers et al. "Fiber-optic biosensors based on total internal-reflection fluorescence," *American Chemical Society* (1992), Ch. 13, pp. 165-173.

Stuart, B. H. et al., "Studies of Adipocere Using Diffuse Reflectance Infrared Spectroscopy," *Vibrational Spectroscopy,* 24:233-242, (2000).

Stubbs, D. D. et al., "Investigation of Cocaine Plumes Using Surface Acoustic Wave Immunoassay Sensors," *Anal. Chem.,* 75:6231-6235, (2003).

Tracqui, A. et al., "Systematic Toxicological Analysis Using HPLC/DAD," *Journal of Forensic Sciences* (1995), vol. 40, No. 2, pp. 254-262.

U.S. Food and Drug Administration, "FDA White Paper, Protecting the Public Health: FDA Pursues and Aggressive Enforcement Strategy," www.fda.gov/oc/whitepapers/enforce.html (Jun. 30, 2003).

U.S. Food and Drug Administration, "New FDA Initiative to Combat Counterfeit Drugs," www.fda.gov/oc/initiatives/counterfeit/backgrounder.html (Jul. 2, 2004).

United States Department of Justice, "Review of the Drug Enforcement Administration's (DEA) Control of the Diversion of Controlled Pharmaceuticals," Report No. I-2002-010 www.usdoj.gov/oig/inspection/DEA/0210/background.htm (Sep. 2002).

VASS, A., "Beyond the Grave — Understanding Human Decomposition," *Microbiology Today,* Nov. 2001, 28:190-192.

Vass, A. et al., "Decomposition Chemistry of Human Remains: A New Methodology for Determining the Postmortem Interval," *J. Forensic Sci.,* (2002), 47(3):542-553.

Vass, A. et al., "Detection of Buried Human Remains Using Bioreporter Fluorescence," U.S. Dept. of Energy Report, Y/NSP-726 (2001).

* cited by examiner

METHOD AND APPARATUS FOR MONITORING RESPIRATORY GASES DURING ANESTHESIA

CROSS REFERENCE TO RELATED APPLICATION

This application is a continuation-in-part of U.S. patent application Ser. No. 10/054,619; filed Jan. 22, 2002, incorporated herein by reference.

FIELD OF INVENTION

The present invention relates to non-invasive monitoring of substance/compound concentrations, and, more particularly, to a method and apparatus for the detection of substance/compound concentrations, including anesthetic agents and respiratory gases, by detecting of concentrations of such agents in exhaled breath and in the breathing circuit.

BACKGROUND INFORMATION

During the administration of anesthesia, anesthesiologists use many sophisticated and expensive devices to monitor the vital signs of and to provide respiratory and cardiovascular support for patients undergoing surgical procedures. Such monitors provide the anesthesiologist with information about the patient's physiologic status and verify that the appropriate concentrations of delivered gases are administered.

Anesthesia can be achieved by using either inhalational or intravenous (IV) anesthetics, or combination of both. Inhalation anesthetics are substances that are brought into the body via the lungs and are distributed with the blood into the different tissues. The main target of inhalation anesthetics (or so-called volatile anesthetics) is the brain. Some commonly used inhalational anesthetics include enflurane, halothane, isoflurane, sevoflurane, desflurane, and nitrous oxide. Older volatile anesthetics include ether, chloroform, and methoxyflurane. Intravenous (IV) anesthetics frequently used clinically are barbiturates, opioids, benzodiazepines, ketamine, etomidate, and propofol. Currently, however, volatile anesthetics are seldom used alone. Rather, a combination of inhalation anesthetics and intravenous drugs are administered, in a process known as "balanced anesthesia." During administration of balanced anesthesia, for example, opioids are administered for analgesia, along with neuromuscular blockers for relaxation, anesthetic vapors for unconsciousness and benzodiazepines for amnesia.

Inhalational Anesthetics

With inhalation agents, the concentration of drug delivered is metered and the variation between patients in the depth of anesthesia resulting from known concentrations of inhaled agents is relatively narrow, permitting the anesthesiologist to confidently assume a particular level of anesthesia based on the concentration of anesthetic gas delivered.

Monitors used during the administration of inhalational anesthesia generally display inspired and exhaled gas concentrations. Most use side-stream monitoring wherein gas samples are aspirated from the breathing circuit through long tubing lines. A water trap, desiccant and/or filter may be used to remove water vapor and condensation from the sample. Gas samples are aspirated into the monitor at a low rate to minimize the amount of gas removed from the breathing circuit and, therefore, the patient's tidal volume. These gas monitors continuously sample and measure inspired and exhaled (end-tidal) concentrations of respiratory gases. The monitored gases are both the physiologic gases found in the exhaled breath of patients (oxygen, carbon dioxide, and nitrogen), as well as those administered to the patient by the anesthesiologist in order to induce and maintain analgesia and anesthesia.

There are a number of techniques to monitor respiratory gases, including mass spectroscopy, Raman spectroscopy, IR—light spectroscopy, IR—photo acoustics, piezoelectric (U.S. Pat. No. 4,399,686 to Kindlund), resonance, polarography, fuel cell, paramagnetic analysis, and magnetoacoustics. Infrared detector systems seem to be the most commonly used systems to monitor gas concentrations.

A major disadvantage of conventional gas monitors is that they only determine the concentrations of certain types of gases or a limited number of gases and most do not measure $N_2$. These monitors are also fragile, expensive and require frequent calibration and maintenance. For this reason, not all purchasers of anesthesia machines buy anesthesia gas monitors and therefore, rely on anesthesia gas vaporizers to control anesthetic gas concentration. Unfortunately, these vaporizers frequently go out of calibration and the anesthesiologist may administer too much or too little anesthesia.

Intravenous (IV) Anesthetics

Another method of providing anesthesia includes IV anesthetics. At present, a major impediment to the wider use of IV anesthetics, rather than inhaled anesthetics, has been the inability to precisely determine the quantity of drug required to provide a sufficient "depth of anesthesia" without accumulating an excessive amount.

Propofol, for example, is an agent that is widely used as a short acting IV anesthetic. Its physiochemical properties are hydrophobic and volatile. It is usually administered as a constant IV infusion in order to deliver and maintain a specific plasma concentration. Although the metabolism is mainly hepatic and rapid, there is significant interpatient variability in the plasma concentration achieved with a known dose. However, the depth of anesthesia for a known plasma concentration is far less variable and it is therefore highly desirable to be able to evaluate plasma concentrations in real time to accurately maintain anesthetic efficacy. ["A Simple Method for Detecting Plasma Propofol," Akihiko Fujita, MD, et al., Feb. 25, 2000, International Anesthesia Research Society]. The authors describe a means to measure plasma rather than total propofol using headspace—GC with solid phase microextraction. This is preferable since plasma (free) propofol is responsible for the anesthetic effect. Prior methods of monitoring propofol concentration in blood include high-performance liquid chromatography (HPLC) and gas chromatography (GC). It has been reported that 97%–99% of propofol is bound with albumin and red blood cells after IV injection, and the remainder exists in blood as a free type. HPLC and GC detect the total propofol concentration, which does not correlate as well with the anesthetic effect as the plasma propofol level.

Propofol may also be monitored in urine. Metabolic processes control the clearance of propofol from the body, with the liver being the principal eliminating organ. ["Firstpass Uptake and Pulmonary Clearance of Propofol," Jette Kuipers, et al., Anesthesiology, V91, No.6, December 1999]. In a study, 88% of the dose of propofol was recovered in urine as hydroxylated and conjugated metabolites.

The aim of any dosage regimen in anesthesia is to titrate the delivery rate of a drug to achieve the desired pharmacolgic effect for any individual patient while minimizing the unwanted toxic side effects. Certain drugs such as propofol, afentanil and remifentanil have a close relationship between blood concentration and effect; thus, the administration of the drug can be improved by basing the dosage regimen on the pharmacokinetics of the agent. [Kenny, Gavin, *Target-Controlled Infusions—Pharmacokinetics and Pharmodynamic Variations*, http://www.anaesthesiologie.med.unier-langen.de/esctaic97/a_Kenny.htm]. Target controlled infusion (TCI) is one means for administering an intravenous anesthesia agent using a computer to control the infusion pump. Using a computer with a pharmacokinetic program permits control of a desired plasma concentration of an agent, such as propofol. The systems do not sample the blood in real-time, but use previously acquired population kinetics to provide a best estimate of the predicted blood concentration. However, even if TCI systems produced the exact target concentrations of blood concentration, it would not be possible to know if that concentration was satisfactory for each individual patient and for different points during the surgical procedure.

Among the technologies used to process and monitor electrical brain signal is BIS (Bispectral Index Monitor) monitoring of the EEG. It is an indirect monitor of depth of anesthesia. The BIS monitor translates EEG waves from the brain into a single number—depicting the depth of anesthesia on a scale from 1 to 100. In addition, neural networks have been used to classify sedation concentration from the power spectrum of the EEG signal. However, this technology is costly and not entirely predictive.

Artificial neural networks have also been developed which use the patient's age, weight, heart rate, respiratory rate, and blood pressure to predict depth of anesthesia. The networks integrate physiological signals and extract meaningful information. Certain systems use mid-latency auditory evoked potentials (MLAEP) which are wavelet transformed and fed into an artificial neural network for classification in determining the anesthesia depth. [Depth of Anesthesia Estimating & Propofol Delivery System, by Johnnie W. Huang, et al., Aug. 1, 1996, http://www.rpi.edu/~royr/roy_descpt.html].

An apparatus and method for total intravenous anesthesia delivery is also disclosed in U.S. Pat. No. 6,186,977 to Andrews. This patent describes a method in which the patient is monitored using at least one of electrocardiogram (EKG), a blood oxygen monitor, a blood carbon dioxide monitor, inspiration/expiration oxygen, inspiration/expiration carbon dioxide, a blood pressure monitor, a pulse rate monitor, a respiration rate monitor, and a patient temperature monitor.

Combination Inhalational and Intravenous (IV) Anesthetics

As previously stated, anesthesia can be achieved by using either inhalational or intravenous (IV) anesthetics, or combination of both ("balanced anesthesia"). Monitoring techniques for inhalational and intravenous anesthesia differ because of the nature of the drug delivery. Monitors for inhalational anesthesia delivery generally comprise systems that monitor the breathing circuit. Monitors for IV anesthesia generally comprise physiologic monitoring of the patient. Based on this bifurcation of monitoring systems, anesthesiologists must utilize separate systems when switching between drug delivery methods or when utilizing a combination of methods.

Accordingly, there is a need in the art for a monitoring system that determines concentration of both intravenous and inhalational anesthetics, especially during the delivery of "balanced anesthesia."

BRIEF SUMMARY OF THE INVENTION

The present invention solves the needs in the art by providing a method and apparatus for non-invasive monitoring of substance/compound concentration in both blood and in breathing circuits (such as anesthesia machine circuits), and, more particularly, to a method and apparatus for the detection, quantitation and trending of IV and/or inhalational delivered drug concentration utilizing sensors. The method includes measuring both exhaled breath concentrations of intravenous and inhalational anesthetics, and also the circuit concentration of inhalational anesthetic gases. The method includes the steps of both measuring the circuit concentration and measuring the concentration of one or more components in the exhaled breath. These measured components can then be used to quantitate the concentration of anesthetics in the circuit (such as halothane, isoflurane, servoflurane, desflurane and enflurane) and to detect, quantitate, and trend the delivered drug, and ultimately determine depth of anesthesia.

A variety of systems have been developed to collect and monitor exhaled breath components, particularly gases. For example, U.S. Pat. No. 6,010,459 to Silkoff describes a method and apparatus for the measurement of components of exhaled breath in humans. Various other apparatus for collecting and analyzing expired breath include the breath sampler of Glaser et al, U.S. Pat. No. 5,081,871; the apparatus of Kenny et al, U.S. Pat. No. 5,042,501; the apparatus for measuring expired breath of infants of Osborn, U.S. Pat. No. 4,202,352; the blood alcohol concentration measuring from respiratory air method of Ekstrom, U.S. Pat. No. 5,971,937, and the instrument for parallel analysis of metabolites in human urine and expired air of Mitsui et al., U.S. Pat. No. 4,734,777. Pulmonary diagnostic systems including computerized data analysis components also are known, e.g., Snow et al., U.S. Pat. No. 4,796,639.

One particular application of the present invention is for predicting the depth of anesthesia utilizing a breath detection system. It has been shown that there is a good correlation between blood concentration of anesthetic agents (e.g., propofol) and depth of anesthesia.

Since there is no direct on-line method to continuously monitor blood concentration of agents, in that the blood and exhaled concentration are relatively proportional, the method of the present invention will provide a more predictive method to monitor depth of anesthesia by monitoring breath rather than blood.

The method of the present invention may also be used to monitor perflubron concentration. Emulsified perflubron is one of a class of compounds used to deliver oxygen in anemic patients as a substitute for hemoglobin.

The invention apparatus provides a device for measuring components of exhaled breath of a subject in the methods described above. This device includes sensor technology; such as the commercial devices referred to as "artificial noses" or "electronic noses" to non-invasively monitor such concentration. Other sensors may include any of those well known in the art such as metal-insulator-metal ensemble (MIME) sensors, cross-reactive optical microsensor arrays, and fluorescent polymer films, surface enhanced Raman spectroscopy (SERS), semiconductor gas sensor technology, conductive polymer gas sensor technology, surface acoustic wave gas sensor technology, aptamers (aptamer biosensors), and amplifying fluorescent polymer (AFP) sensors. The invention further includes a reporting system capable of tracking concentration (remote or proximate) and providing the necessary outputs, controls, and alerts.

In one example, the present invention would be used during delivery of anesthesia to monitor and control delivery of anesthesia by measuring anesthetic concentration in both the breathing circuit (for inhalational anesthetics) and in exhaled breath.

The preferred device of the present invention includes two parts: 1) the breathing circuit sensor and 2) the expired breath sensor. The breathing circuit sensor includes a sensor having a surface exposed to the gas stream and comprises a material selectively absorptive of a chemical vapor or group of vapors. The expired breath sensor includes a sensor having a surface exposed to the patient's breath and/or airway and also comprises a material selectively absorptive of a chemical vapor or group of vapors. These sensors are coupled to an analyzer(s) for producing an electrical signal indicative of the presence of the vapors. The analyzer is further operative to determine the approximate concentration of the vapors, display results, signal alarms, etc.

The sensor is preferably a surface acoustic wave device, such as that disclosed in pending U.S. application Ser. No. 09/708,789 entitled "Marker Detection Method and Apparatus to Monitor Drug Compliance" of which applicant is a co-inventor, the description of which is incorporated herein by reference. The sensor device disclosed in U.S. Pat. No. 5,945,069 may also be utilized.

In one embodiment, the device detects a target substance (anesthetic gases and/or physiologic gases) in both the breathing circuit and in expired breath using the following components: (a) surface-acoustic wave sensor(s) capable of detecting the presence of the target substance, wherein the sensor responds to the target substance by a shift in the resonant frequency; (b) oscillator circuit(s) having the sensor as an active feedback element; (c) frequency counter(s) in communication with the oscillator circuit(s) to measure oscilation frequency which corresponds to resonant frequency of the sensor(s); and (d) a processor for comparing the oscillation frequency with a previously measured oscillation frequency of the target substance and determining presence and concentration of the target substance therefrom.

In another embodiment, the device detects a target substance (anesthetic gases and/or physiologic gases) in both the breathing circuit and in expired breath using the following components: (a) sensor(s) having an array of polymers capable of detecting the presence of the target substance, wherein the sensor(s) responds to the target substance by changing the resistance in each polymer resulting in a pattern change in the sensor array; (b) a processor for receiving the change in resistance, comparing the change in resistance with a previously measured change in resistance, and identifying the presence of the target substance from the pattern change and the concentration of the substance from the amplitude. The processor can include a neural network for comparing the change in resistance with a previously measured change in resistance to find a best match.

In another embodiment, the invention includes a method of monitoring a patient during administration of anesthesia wherein the patient is connected to a breathing circuit. In the method, a first sensor is exposed to inspired gases, wherein at least one inspired gas is an anesthetic agent; a second sensor is exposed to expired gases; one or more target substances is detected with the sensors; and concentration of the target substances is determined.

In another embodiment, the invention includes an anesthetic agent delivery system for delivering balanced anesthesia to a patient through a breathing circuit and an IV which includes: (1) an anesthetic gas supply having a controller for controlling the amount of volatile anesthetic agent provided by the supply to the breathing circuit; (2) an intravenous anesthetic agent supply having a controller for controlling the amount of IV anesthetic agent administered to the patient intravenously; (3) an inspired gas analyzer for analyzing the concentration of anesthetic gas in the breathing circuit; (4) an expired gas analyzer for analyzing the patient's breath for concentration of at least one substance indicative of anesthetic agent concentrations in the patient's bloodstream that provides at least one signal to indicate the anesthetic agent concentration delivered to the patient; and (5) a system controller connected to each of the anesthetic supplies which receives the signal and controls the amount of anesthetic agents administered based on the signal.

In still a further embodiment, the invention includes an apparatus for administering balanced anesthesia to a patient including: (1) at least one supply of at least one intravenous anesthetic agent; (2) intravenous delivery means for controllably delivering the intravenous anesthetic agent to the patent; (3) at least one supply of at least one inhalational anesthetic agent; (4) a breathing circuit for delivery of said inhalational anesthetic agent; (5) an inspired gas analyzer for analyzing gas in the breathing circuit for the inhalational agent; (6) an expired gas analyzer for analyzing the patient's breath for concentration of at least one substance indicative of anesthetic agents in the patient's bloodstream that provides a signal to indicate anesthetic agent concentration delivered to the patient; (7) a system controller connected to the intravenous delivery means which receives the signal and controls the amount of anesthetic agent based on the signal; and (8) a system controller connected to the breathing circuit which receives the signal and controls the amount of anesthetic agent based on the signal.

Another embodiment includes a device for detecting target substances in a breathing circuit including: (1) at least one surface-acoustic wave sensor capable of detecting the presence of the target substance in inspired and/or expired gas, wherein the sensor responds to the target substance by a shift in the resonant frequency; (2) an oscillator circuit having the sensor as an active feedback element; (3) a frequency counter in communication with the oscillator circuit to measure oscillation frequency which corresponds to resonant frequency of the sensor; and (4) a processor for comparing the oscillation frequency with a previously measured oscillation frequency of the target substance and determining presence and concentration of the target substance therefrom.

Another embodiment includes a device for detecting target substances in a breathing circuit including: (1) a sensor having an array of polymers capable of detecting the presence of the target substance in inspired and/or expired gas, wherein the sensor responds to the target substance by changing the resistance in each polymer resulting in a pattern change in the sensor array; (2) a processor for receiving the change in resistance, comparing the change in resistance with a previously measured change in resistance, and identifying the presence of the target substance from the pattern change and the concentration of the substance from the amplitude.

Moreover, sensing antibiotics with the exhaled breath detection method of the present invention, would allow for use of the method as a surrogate for blood antibiotic concentration. This would also be true for a wide range of medications for which blood concentration would be valuable. Exhaled breath detection using the method of the present invention may also evaluate pharmacodynamics and pharmacokinetics for both drug studies and in individual patients. Moreover, it may be used to sense endogenous compounds such as glucose, ketones and electrolytes which are normally found in blood.

The invention also includes a method of determining the rate of washout of a target substance (anesthetic gases) by (a) obtaining a sample of expired breath at a first interval; (b) analyzing the sample with sensor technology to determine the concentration of the substance; (c) obtaining at least one additional sample of expired breath at a later interval; (d) analyzing said additional sample with sensor technology to determine the concentration of said substance; and (e) comparing the concentration of the first sample with the concentration of additional samples to determine rate of washout of the target substance.

Therefore, it is an object of the present invention to non-invasively monitor substance concentration by methods including, but not limited to, sensor technology (e.g., silicon chip technology). A resulting advantage is the ability to monitor such concentration in a more cost effective and frequent manner, especially during balanced anesthesia where inhalational and IV anesthetics are administered. This method may replace the invasive practice of drawing blood to measure concentration. Moreover, measurement of medications (and other substances) in exhaled breath may prove to be a major advance in monitoring a variety of drugs, compounds, naturally occurring metabolites, and molecules.

The invention will now be described, by way of example and not by way of limitation, with reference to the accompanying sheets of drawings and other objects, features and advantages of the invention will be apparent from this detailed disclosure and from the appended claims. All patents, patent applications, provisional applications, and publications referred to or cited herein, or from which a claim for benefit of priority has been made, are incorporated by reference in their entirety to the extent they are not inconsistent with the explicit teachings of this specification.

DETAILED DESCRIPTION OF THE INVENTION

The present invention provides a method and apparatus for non-invasive monitoring substance/compound concentration by utilizing sensors that detect and measure concentration in expired breath and in the breathing circuit. As such, the invention is extremely useful in "balanced anesthesia" delivery where both inhalational and IV anesthetics are used. The invention further includes a method and apparatus for detecting the depth of anesthesia utilizing the breath detection system of the present invention.

Gas Sensor Technology

The preferred sensor technology of the present invention is based on surface acoustic wave (SAW) sensors. These sensors oscillate at high frequencies and respond to perturbations proportional to the mass load of certain molecules. This occurs in the vapor phase on the sensor surface. The resulting frequency shift is detected and measured by a computer. Usually, an array of sensors (4–6) is used; each coated with a different chemoselective polymer that selectively binds and/or absorbs vapors of specific classes of molecules. The resulting array, or "signature," identifies specific compounds.

Figure 1:
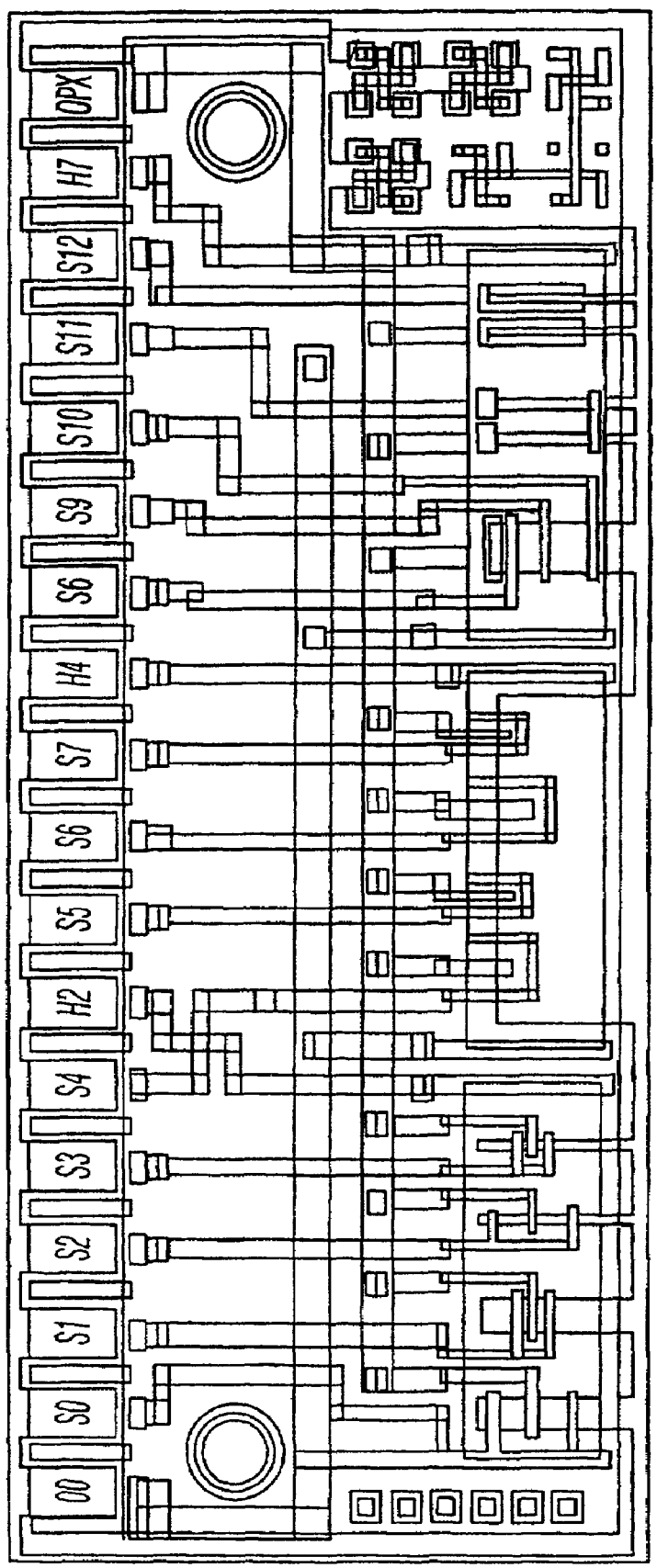
FIG. 1 shows a gas sensor chip that may be utilized as a sensor for the present invention.

The invention preferably utilizes gas sensor technology, such as the commercial devices referred to as "artificial noses" or "electronic noses," to non-invasively monitor concentration (FIG. 1). An "electronic or artificial nose" is an instrument, which comprises a sampling system, an array of chemical gas sensors with differing selectivity, and a computer with an appropriate pattern-classification algorithm, capable of qualitative and/or quantitative analysis of simple or complex gases, vapors, or odors. Electronic noses have been used mostly in the food, wine and perfume industry where their sensitivity makes it possible to distinguish between grapefruit oil and orange oil and identify spoilage in perishable foods before the odor is evident to the human nose. There has been little medical-based research and application; however, recent examples demonstrate the power of this non-invasive technique. Electronic noses have determined the presence of bacterial infection in the lungs simply by analyzing the exhaled gases of patients for odors specific to particular bacteria [Hanson C W, Steinberger H A: The use of a novel electronic nose to diagnose the presence of intrapulmonary infection. *Anesthesiology*, V87, No. 3A, Abstract A269, September 1997]. Also a genitourinary clinic has utilized an electronic nose to screen for, and detect bacterial vaginosis, with a 94% success rate after training [Chandiok S, et al.: Screening for bacterial vaginosis: a novel application of artificial nose technology. Journal of Clinical Pathology, 50(9):790–1, 1997]. Specific bacterial species can also be identified with the electronic nose based on special odors produced by the organisms [Parry A D et al.: Leg ulcer odor detection identifies betahaemolytic streptococcal infection. Journal of Wound Care, 4:404–406, 1995].

A number of patents which describe gas sensor technology include the following: U.S. Pat. No. 5,945,069 to Buchler, entitled "Gas sensor test chip;" U.S. Pat. No. 5,918,257 to Mifsud et al., entitled "Method and devices for the detection of odorous substances and applications"; U.S. Pat. No. 4,938,928 to Koda et al., entitled "Gas sensor"; U.S. Pat. No. 4,992,244 to Grate, entitled "Films of dithiolene complexes in gas-detecting microsensors"; U.S. Pat. No. 5,034,192 to Wrighton et al., entitled "Molecule-based microelectronic devices"; U.S. Pat. No. 5,071,770 to Kolesar, Jr., entitled "Method for gaseous component identification with #3 polymeric film;" U.S. Pat. No. 5,145,645 to Zakin et al., entitled "Conductive polymer selective species sensor;" U.S. Pat. No. 5,252,292 to Hirata et al., entitled "Ammonia sensor;" U.S. Pat. No. 5,605,612 to Park et al., entitled "Gas sensor and manufacturing method of the same;" U.S. Pat. No. 5,756,879 to Yamagishi et al., entitled "Volatile organic compound sensors;" U.S. Pat. No. 5,783, 154 to Althainz et al., entitled "Sensor for reducing or oxidizing gases;" U.S. Pat. No. 5,830,412 to Kimura et al., entitled "Sensor device, and disaster prevention system and electronic equipment each having sensor device incorporated therein," and U.S. Pat. Nos. 4,361,026; 4,399,686; 5,060,506; 5,325,704; 5,351,522; 5,528,924; 5,900,552; 6,085,576; 6,244,096; 6,305,212, and European Patent Nos. EP 0565610, EP 0760076, all of which are incorporated herein by reference in their entirety.

Figure 2:
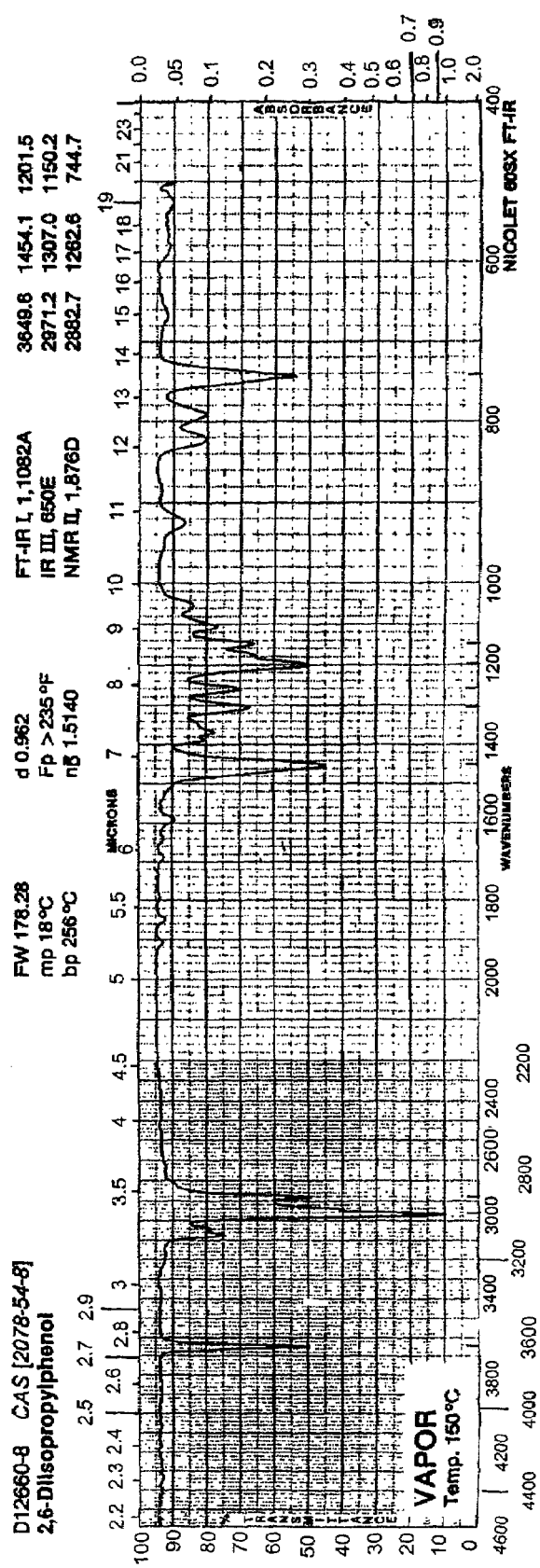
FIG. 2 shows the FT-IR signal for propofol.

Other sensors suitable for the present invention include, but are not limited to, metal-insulator-metal ensemble (MIME) sensors, cross-reactive optical microsensor arrays, and fluorescent polymer films, surface enhanced raman spectroscopy (SERS), diode lasers, selected ion flow tubes, proton transfer reaction mass spectrometry, metal oxide sensors (MOS), non-dispersive infrared spectrometer, bulk acoustic wave sensors, colorimetric tubes, infrared spectroscopy (FIG. 2 represents the FT-IR signal for propofol (2,6-diisopropylphenol)).

Recent developments in the field of detection include, but are not limited to, semiconductive gas sensors, mass spectrometers, IR or UV or visible or fluorescence spectrophotometers. The substances change the electrical properties of the semiconductors by making their electrical resistance vary, and the measurement of these variations allows one to determine the concentration of substances. These methods and apparatus used for detecting substances use a relatively brief detection time, of around a few seconds.

Other recent gas sensor technologies included in the present invention include apparatus having conductive-polymer gas-sensors ("polymeric"), apparatus having surface-acoustic-wave (SAW) gas-sensors, and aptamers (aptamer biosensors), and amplifying fluorescent polymer (AFP) sensors.

The conductive-polymer gas-sensors (also referred to as "chemoresistors") have a film made of a conductive polymer sensitive to the molecules of odorous substances. On contact with the molecules, the electric resistance of the sensors changes and the measurement of the variation of this resistance enables the concentration of substances to be determined. An advantage of this type of sensor is that it functions at temperatures close to room temperature. One can also obtain, according to the chosen conductive polymer, different sensitivities for detecting different substances.

Polymeric gas sensors can be built into an array of sensors, where each sensor is designed to respond differently to different gases and augment the selectivity of the substances.

The surface-acoustic-wave (SAW) gas-sensors generally include a substrate with piezoelectric characteristics covered by a polymer coating that is able to selectively absorb the substances. The variation of the resulting mass leads to a variation of its resonant frequency. This type of sensor allows for very good mass-volume measures of the substances. In the SAW device, the substrate is used to propagate a surface acoustic wave between sets of interdigitated electrodes. The chemoselective material is coated on the surface of the transducer. When a chemical analyte interacts with a chemoselective material coated on the substrate, the interaction results in a change in the SAW properties such as the amplitude of velocity of the propagated wave. The detectable changes in the characteristics of the wave indicate the presence of the chemical analyte. SAW devices are described in numerous patents and publications, including U.S. Pat. No. 4,312,228 to Wohltjen and U.S. Pat. No. 4,895,017 to Pyke, and Groves W A, et al.: Analyzing organic vapors in exhaled breath using surface acoustic wave sensor array with preconcentration: Selection and characterization of the preconcentrator adsorbent, *Analytica Chimica Acta* 371 (1988) 131–143, all of which are incorporated herein by reference. Other types of chemical sensors known in the art that use chemoselective coatings applicable to the operation of the present invention include bulk acoustic wave (BAW) devices, plate acoustic wave devices, interdigitated microelectrode (IME) devices, and optical waveguide (OW) devices, electrochemical sensors, optical sensors, and electrically conducting sensors.

Most current technologies for creating large area films of polymers and biomaterials involve the spinning, spraying, or dipping of a substrate into a solution of the macromolecule and a volatile solvent. These methods coat the entire substrate. There are also techniques such as microcontact printing and hydrogel stamping that enable small areas of biomolecular and polymer monolayers to be patterned. Other techniques, such as pulsed laser deposition (PLD), may be used. By this method, a target comprising the stoichiometric chemical composition of the material to be used for the coating is ablated by means of a pulsed laser, forming a plume of ablated material that becomes deposited on the substrate.

Polymer thin films, using a new laser based technique developed by researchers at the Naval Research Laboratory called Matrix Assisted Pulsed Laser Evaporation (MAPLE), have recently been shown to increase sensitivity and specificity of chemoselective Surface Acoustic Wave vapor sensors. A variation of this technique, Pulsed Laser Assisted Surface Functionalization (PLASF) is preferably used to design compound specific biosensor coatings with increased sensitivity for the present invention. PLASF produces similar thin films for sensor applications with bound receptors or antibodies for biosensor applications. By providing improved SAW biosensor response by eliminating film imperfections induced by solvent evaporation and detecting molecular attachments to specific antibodies, high sensitivity and specificity is possible.

Certain extremely sensitive, commercial off-the-shelf (COTS) electronic noses, such as those provided by Cyrano Sciences, Inc. ("CSI") (e.g., CSI's Portable Electronic Nose and CSI's Nose-Chip integrated circuit for odor-sensing—U.S. Pat. No. 5,945,069—FIG. 1), may be used in the method of the present invention to monitor the exhaled breath from a patient. These devices offer minimal cycle time, can detect multiple compounds, can work in almost any environment without special sample preparation or isolation conditions, and do not require advanced sensor design or cleansing between tests.

Other technologies and methods are contemplated herein for detection of substances. For example, a patient's breath can be captured into a container (vessel) for later analysis at a central instrument such as a mass spectrometer.

Aptamers (aptamer biosensors) maybe utilized in the present invention for sensing. Certain types of aptamer biosensors are resonant oscillating quartz sensors which can detect minute changes in resonance frequence due to modulations of mass of the oscillating system which results from a binding or dissociation event. Similarly, molecular beacons (MB) and molecular beacon aptamers (MBA) employ fluorescence resonance energy transfer based methods to provide fluorescence signal increases in the presence of particular target sequences. See also, Stojanovic, Milan N., de Prada, Paloma, and Landry, Donald W., "Aptamer-Based Folding Fluorescent Sensor for Cocaine" J. Am. Chem. Soc. 2001, 123, 4928–4931 (2001); Jayasena, Sumedha D., "Aptamers: An Emerging Class of Molecules That Rival Antibodies of Diagnostics, Clinical Chemistry 45:9, 1628–1650 (1999).

Similarly, amplifying fluorescent polymer (AFP) sensors may be utilized in the present invention for sensing. AFP sensors are an extremely sensitive and highly selective chemosensors that use amplifying fluorescent polymers (AFPs). When vapors bind to thin films of the polymers, the fluorescence of the films decreases. A single molecular binding event quenches the fluorescence of many polymer repeat units, resulting in an amplification of the quenching. Analyte binding to the films is reversible, so the films can be reused.

Figure 3A:
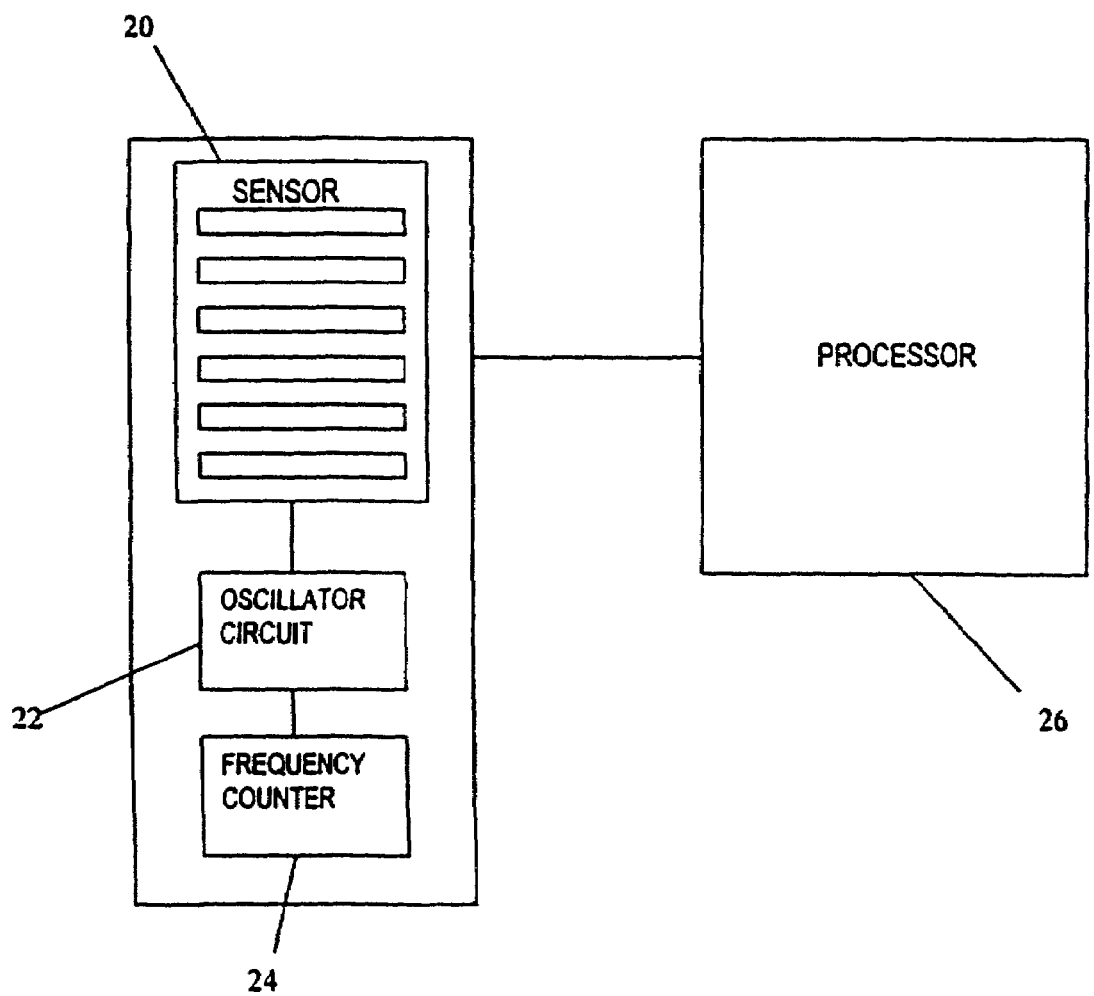
FIG. 3a shows a gas sensor system in accordance with one embodiment of the invention.

FIG. 3a shows an example of a device for detecting substances (anesthetic gases, drugs, and/or physiologic gases) in both the breathing circuit and in expired breath having the following components: (a) surface-acoustic wave sensor(s) 20 capable of detecting the presence of the target substance, wherein the sensor responds to the target substance by a shift in the resonant frequency; (b) oscillator circuit(s) 22 having the sensor(s) as an active feedback element; (c) frequency counter(s) 24 in communication with the oscillator circuit to measure oscillation frequency which corresponds to resonant frequency of the sensor(s); and (d) a processor 26 for comparing the oscillation frequency with a previously measured oscillation frequency of the target substance and determining presence and concentration of the target substance therefrom. The sensor can include measuring circuitry (not shown) and an output device (not shown) can also be included (e.g., screen display, audible output, printer).

The processor can include a neural network (not shown) for pattern recognition. Artificial Neural Networks ANNs are self learning; the more data presented, the more discriminating the instrument becomes. By running many standard samples and storing results in computer memory, the application of ANN enables the device to "understand" the significance of the sensor array outputs better and to use this information for future analysis. "Learning" is achieved by varying the emphasis, or weight, that is placed on the output of one sensor versus another. The learning process is based on the mathematical, or "Euclidean," distance between data sets. Large Euclidean distances represent significant differences in sample-to-sample aroma characteristics.

Figure 3B:
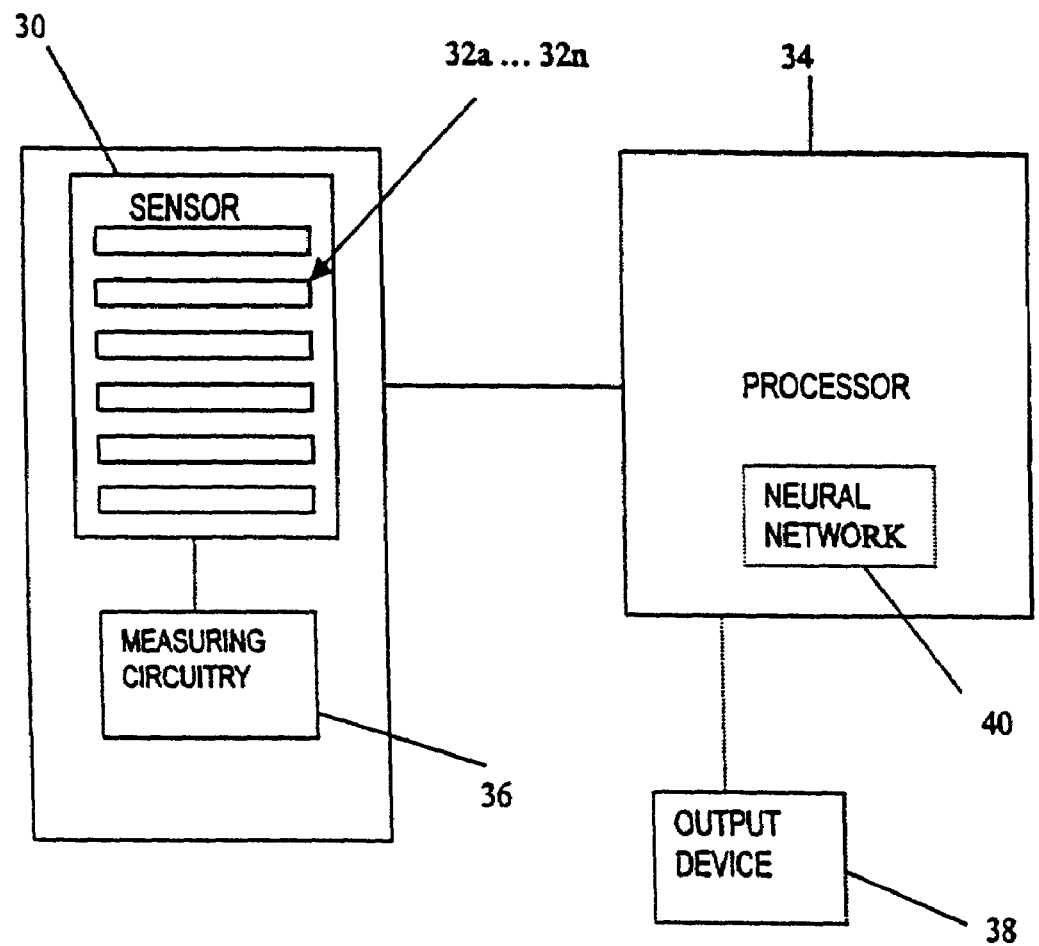
FIG. 3b shows a gas sensor system in accordance with another embodiment of the invention.

In an alternate embodiment, FIG. 3b shows an example of a device for detecting a target substance (anesthetic gases, drugs, and/or physiologic gases) having the following components: (a) sensor(s) 30 having an array of polymers 32a–32n capable of detecting the presence of the target substance, wherein the sensor responds to the target substance by changing the resistance in each polymer resulting in a pattern change in the sensor array; (b) a processor 34 for receiving the change in resistance, comparing the change in resistance with a previously measured change in resistance, and identifying the presence of the target substance from the pattern change and the concentration of the substance from the amplitude. The processor can include a neural network 40 for comparing the change in resistance with a previously measured change in resistance to find a best match (pattern recognition). The sensor can include measuring circuitry 36 and an output device 38 can also be included (e.g., screen display, audible output, printer).

Intravenous IV Anesthesia Delivery

During intravenous anesthesia, anesthetic agents are administered directly into a patient's bloodstream rather than administering gases through a breathing circuit. The administered drug may bind to proteins circulating in the blood, be absorbed into fat or exist in a "free" form. Drug bound to protein or absorbed in fat does not produce a pharmacological effect and exists in equilibrium with unbound drug. Numerous factors, including competition for binding sites on the protein from other drugs, the amount of fat in the body and the amount of protein produced, determine the equilibrium between bound and unbound drug. Unbound drug may participate directly in the pharmacological effect or be metabolized into a drug that produces the effect. Metabolism of the active drug often leads to its removal from the bloodstream and termination of its effect. The drug effect can also be terminated by the excretion of the free drug. Free drug or a metabolite can be excreted in the urine or the digestive tract or in exhaled breath. The concentration in the blood (or plasma or serum) of such agents (e.g., propofol, alfentanil and remifentanil) is related to the clinical effect of the agent.

FIG. 2 represents the FT-IR signal for propofol (2,6-diisopropylphenol). It has been specifically shown that there is a good correlation between blood concentration of anesthetic agents (e.g., propofol) and depth of anesthesia. Therefore, testing blood concentration is a good indicator of the effect of the agent (depth of anesthesia). Unfortunately, testing blood directly is invasive and time consuming. When a drug or its metabolite is excreted in the breath, the concentration in expired breath is proportional to the free drug or metabolite concentration in the blood and, thus, indicative of depth of anesthesia and/or the rate of drug metabolism. The metabolite measured in exhaled breath may be the active metabolite or a breakdown product of the active drug. As long as there is equilibrium between the active drug and an inactive metabolite excreted in the breath, the activity of the active drug will be known. The method of the present invention takes into account such proportional concentrations and allows for the determination of depth of anesthesia and/or the rate of metabolism of the drug by measuring concentration of unbound substances, agents and/or active metabolites in a patient's breath, see FIG. 4. The proper dosing regimen can thus be determined therefrom.

Generally, the exhalation gas stream comprises sequences or stages. At the beginning of exhalation there is an initial stage, the gas representative thereof coming from an anatomically inactive (deadspace) part of the respiratory system, in other words, from the mouth and upper respiratory tracts. This is followed by a plateau stage. Early in the plateau stage, the gas is a mixture of deadspace and metabolically active gases. The last portion of the exhaled breath comprises nothing but deep lung, so-called alveolar gas. This gas, which comes from the alveoli, is termed end-tidal gas. In one embodiment, the exhaled breath sample is collected at end-tidal breathing. Technology similar to that used for end-tidal carbon dioxide monitoring can be used to determine when the sample is collected. Airway pressure measurements afford another means of collecting samples at the appropriate phase of the respiratory cycle. Single or multiple samples collected by the side stream method are preferable, but if sensor acquisition time is reduced, in-line sampling maybe used. In the former, samples are collected through an adapter at the proximal end of the endotracheal tube and drawn through thin bore tubing to the sensor chamber. Depending on the sample size and detector response time, gas may be collected on successive cycles. With in-line sampling, the sensor is placed proximal to the ET tube directly in the gas stream. Alternatively to sampling end-tidal gas, samples can be taken throughout the exhalation phase of respiration and average value determined and correlated with blood concentration.

Figure 5:
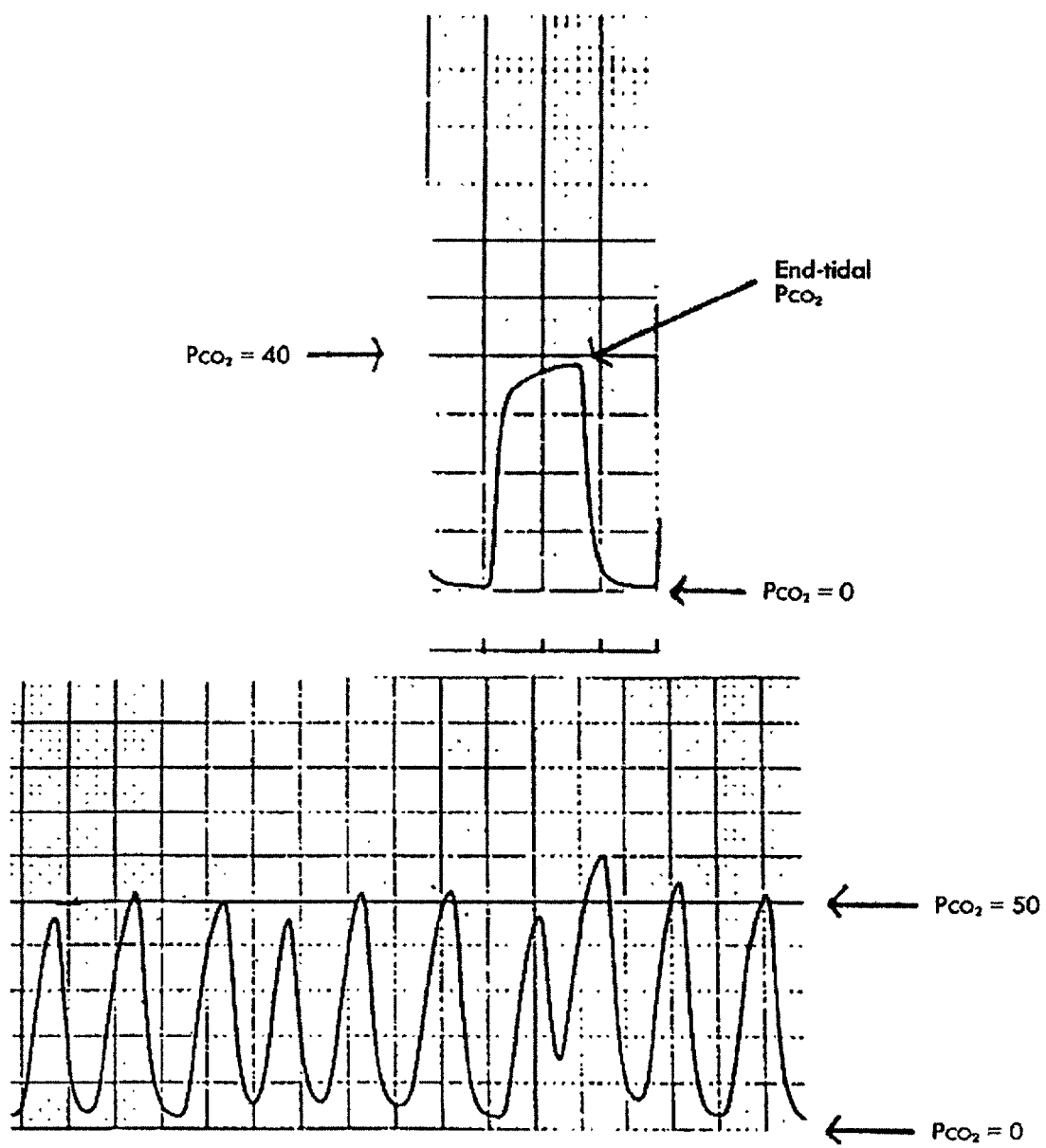
FIG. 5 shows a capnogram of a single respiratory cycle and a capnogram of several breaths from a patient with obstructive lung disease.

Referring now to FIG. 5, the upper frame demonstrates a capnogram of a single respiratory cycle. For accurate blood level correlation, samples are taken at the point labeled "end-tidal $PCO_2$," which reflects the $CO_2$ concentration in the lung. The lower frame shows a capnogram of several breaths from a patient with obstructive lung disease. Again the end-tidal sample correlated best with blood concentration.

Figure 6A:
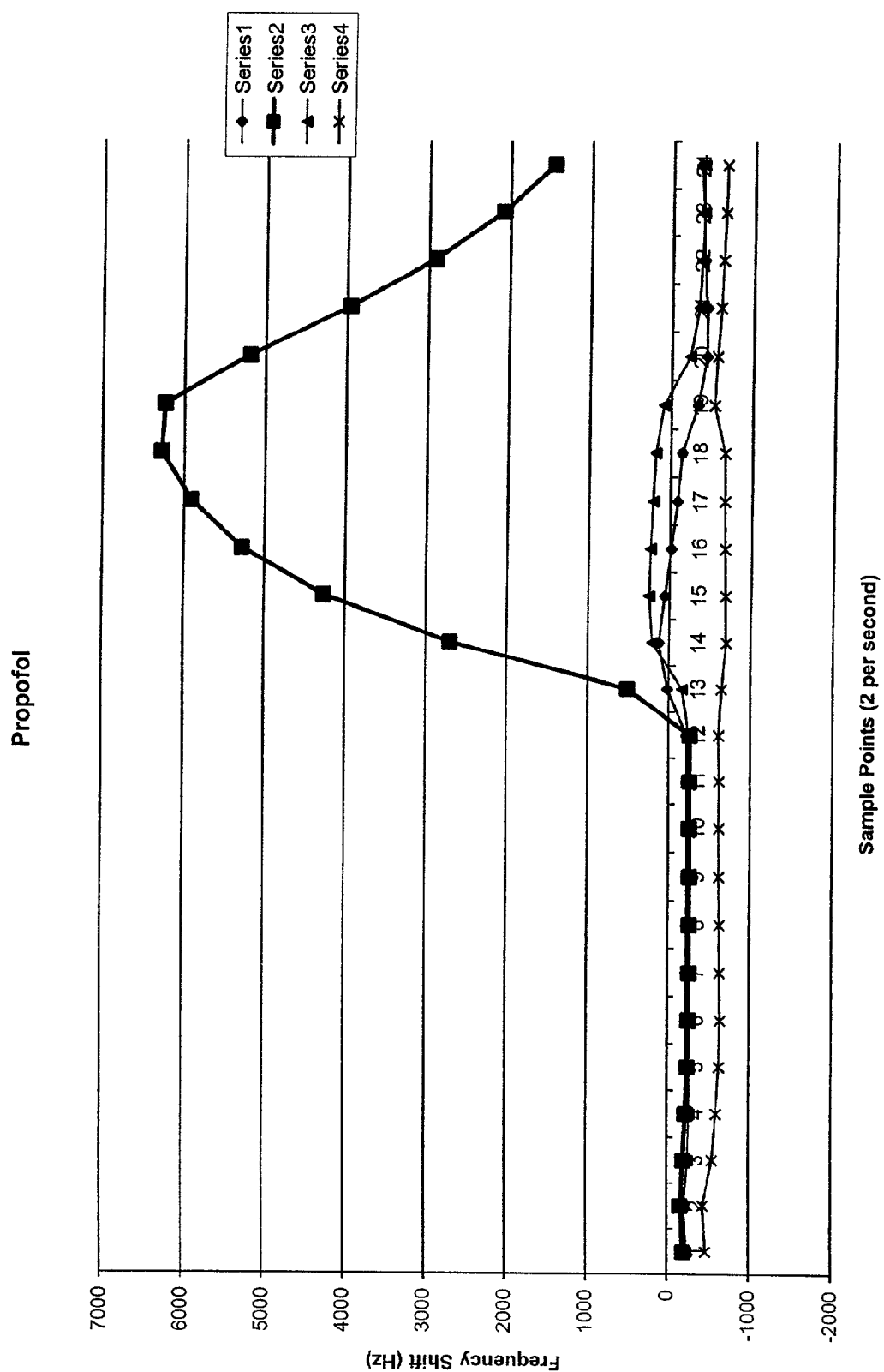
FIG. 6a shows the characteristic signature of propofol.

Referring now to FIG. 6a, the characteristic signature of propofol from a four (4) sensor polymer coated SAW array is shown. In this example, 1 cc of propofol was placed in a "headspace" gas chromatography vial. A 19-gauge hypodermic needle attached to a VaporLab™ gas detector containing the sensor array was inserted into the vial, which was heated to 37° C. , and the "signature" was recorded. The VaporLab™ brand instrument is a hand-held, battery powered SAW based chemical vapor identification instrument suitable for detecting vapors in accordance with the present invention. This instrument is sensitive to volatile and semi-volatile compounds and has a high-stability SAW sensor array that provides orthogonal vapor responses for greater accuracy and discrimination. The device communicates with computers to provide enhanced pattern analysis and report generation. The device can be easily "trained" to remember chemical vapor signature patterns for fast, "on-the-fly" analysis. Note that the "signature" has both amplitude and temporal resolution. In the present invention, vapor concentration measurements of vapors are made by detecting the adsorption of molecules onto the surface of a SAW sensor coated with a polymer thin film. This thin film is specifically coated to provide selectivity and sensitivity to specific vapors. The SAW is inserted as an active feedback element in an oscillator circuit. A frequency counter measures the oscillation frequency, which corresponds to the resonant frequency of the SAW sensor. The response of the SAW sensor to the vapor is measured as a shift in the resonant frequency of the SAW sensor. This configuration requires an oscillator circuit, the coated SAW sensor, and a frequency counter, all of which can be housed on a small printed circuit board.

Figure 6B:
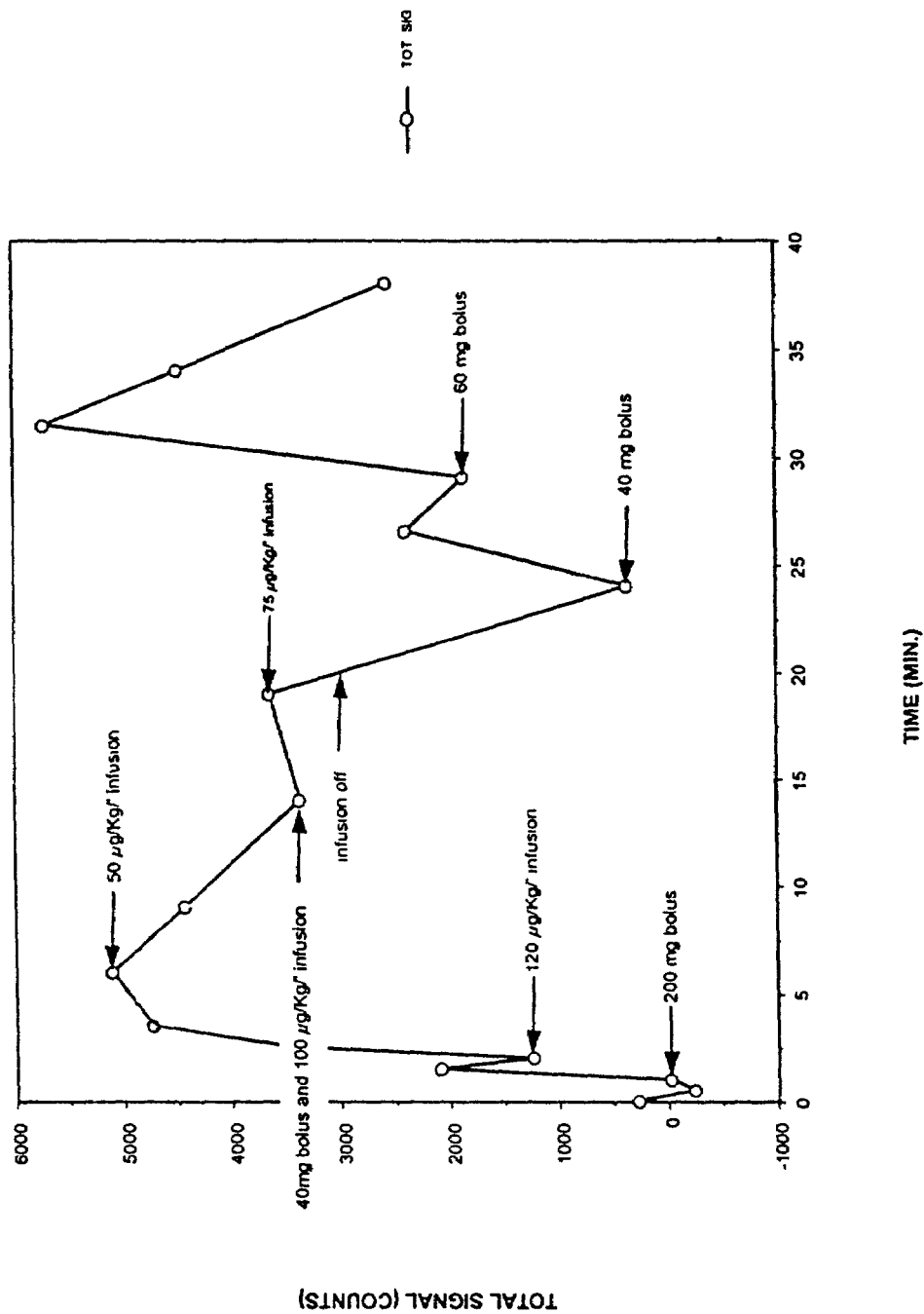
FIG. 6b shows a Propofol relative breath concentration profile of a patient.

FIG. 6b shows an example of a Propofol relative breath concentration profile in a patient.

In another embodiment, samples are collected at the distal end of the endotracheal tube (ETT) through a tube with a separate sampling port. This may improve sampling by allowing a larger sample during each respiratory cycle.

The concentration of an anesthetic agent in the body is regulated both by the amount of the agent administered over a given time period and the rate at which the agent is eliminated from the body (metabolism). The present invention provides the steps of administering an agent to the subject and analyzing exhaled breath of the subject for concentration of unbound substances, active metabolites, or inactive metabolites after a suitable time period; the concentration indicates a characteristic of metabolism of the agent in the subject. The method may further include using a flow sensor to detect starting and completion of exhalation. The method further includes providing results from the analysis and controlling the infusion pump for delivering the intravenous anesthesia agent based on the results. Moreover, a CPU may be provided as a data processing/control unit for automatically detecting the signal from the flow sensor to control sampling of exhaled breath. The CPU may further provide the analysis and control of the infusion pump or other administering means.

Methods for administering the agent are readily understood by those skilled in the art. For example, an infusion pump may be used. Compounds may be also administered parenterally, sublingually, transdermally, by i.v. bolus, and by continuous infusion. A number of suitable agents are available for administration as also known by those skilled in the art (Remifentanil—Glaxo Wellcome, Propofol—Zeneca). Agents may also be those of amnesia, analgesia, muscle relaxation, and sedation agents or a combination thereof. Agents may be administered in an amount for analgesia, conscious sedation, or unconsciousness as known in the art. Patient characteristics may also be monitored during administration of the agent.

Concentration in the blood as measured by the breath analysis of the present invention for free agents or metabolites may indicate when the patient is receiving an anesthetic concentration (a high dose), an analgesic concentration (a low dose), or emerging from anesthesia as a result of a level that allows for full recovery. Even if there is wide variation in the metabolism or response to an anesthetic agent, knowledge of the exhaled breath concentration allows the anesthesiologist to know if the drug is accumulating in the blood, possibly leading to a dangerously deep level of anesthesia and/or a prolonged recovery time: or, the concentration is falling, possibly leading to inadequate anesthesia and premature emergence. Monitoring changes in concentration are, therefore, useful.

In another embodiment, the exhalation air is measured for free agent and/or metabolite concentration either continuously or periodically. From the exhalation air is extracted at least one measured free agent or metabolite concentration value. Numerous types of apparatus may be used to carry out the method of the present invention. In one embodiment, the apparatus includes a conventional flow channel through which exhalation air flows. The flow channel is provided with sensor elements for measuring free agent or metabolite concentration. Furthermore, the apparatus includes necessary output elements for delivering at least a measured concentration result to the operator, if necessary. An alarm mechanism may also be provided. An instrument of similar type is shown in FIGS. 1 and 2 of U.S. Pat. No. 5,971,937 incorporated herein by reference.

In one embodiment, once the level of concentration is measured, it is given numerical value (for example, 50 on a scale of 1 to 100). Should the concentration fall below that value, the new value would be indicative of a decrease in concentration. Should the concentration increase beyond that value, the new value would be indicative of an increase in concentration. This numerical scale would allow for easier monitoring of changes in concentration. The numerical scale would also allow for easier translation into control signals for alarms, outputs, charting, and control of external devices (e.g., infusion pump). The upper and lower limits could be set to indicate thresholds such as from no anesthetic effect to dangerous anesthetic levels.

Figure 4:
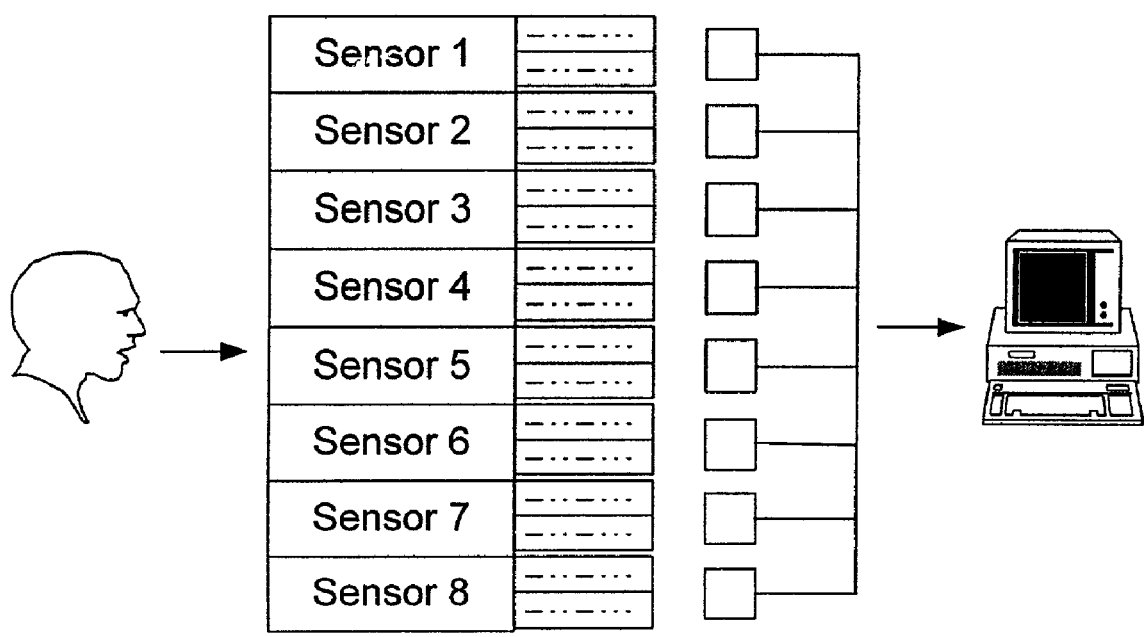
FIG. 4 shows an example of measuring expired breath of a patient utilizing a sensor.

In one embodiment, the device of the present invention may be designed so that patients can exhale via the mouth or nose directly into the device, FIG. 4.

Another preferred electronic nose technology of the present invention comprises an array of polymers, for example, 32 different polymers, each exposed to a substance. Each of the 32 individual polymers swells differently to the odor creating a change in the resistance of that membrane and generating an analog voltage in response to that specific substance ("signature"). The normalized change in resistance can then be transmitted to a processor to identify the type, quantity, and quality of the substance based on the pattern change in the sensor array. The unique response results in a distinct electrical fingerprint that is used to characterize the substance. The pattern of resistance changes of the array is diagnostic of the sample, while the amplitude of the pattern indicates the concentration of the sample.

The responses of the electronic nose to specific substances can be fully characterized using a combination of conventional gas sensor characterization techniques. For example, the sensor can be attached to a computer. The results can be displayed on the computer screen, stored, transmitted, etc. A data analyzer can compare a pattern of response to previously measured and characterized responses from known substances. The matching of those patterns can be performed using a number of techniques, including neural networks. By comparing the analog output from each of the 32 polymers to a "blank" or control, for example, a neural network can establish a pattern that is unique to that substance and subsequently learns to recognize that substance. The particular resistor geometries are selected to optimize the desired response to the particular substance being sensed. The sensor of the present invention is preferably a self-calibrating polymer system suitable for liquid or gas phase biological solutions for a variety of substances simultaneously.

The sensor of the present invention might include integrated circuits (chips) manufactured in a modified vacuum chamber for Pulsed Laser Deposition of polymer coatings. It will operate the simultaneous thin-film deposition wave detection and obtain optimum conditions for high sensitivity of SAW sensors. The morphology and microstructure of biosensor coatings will be characterized as a function of process parameters.

The sensor used in the present invention may be modified so that patients can exhale directly into the device. For example, a mouthpiece or nosepiece will be provided for interfacing a patient with the device to readily transmit the exhaled breath to the sensor (See, e.g., U.S. Pat. No. 5,042,501). The output from the neural network of the modified sensor should be similar when the same patient exhales directly into the device and when the exhaled gases are allowed to dry before they are sampled by the sensor.

The humidity in the exhaled gases represents a problem for certain electronic nose devices (albeit not SAW sensors) that only work with "dry" gases. When using such humidity sensitive devices, the present invention may adapt such electronic nose technology so that a patient can exhale directly into the device with a means to dehumidify the samples. This is accomplished by including a commercial dehumidifier or a heat moisture exchanger (HME), a device designed to prevent desiccation of the airway during ventilation with dry gases. Alternatively, the patient may exhale through their nose which is an anatomical, physiological dehumidifier to prevent dehydration during normal respiration. Alternatively, the sensor device can be fitted with a preconcentrator, which has some of the properties of a GC column. The gas sample is routed through the preconcentrator before being passed over the sensor array. By heating and volatilizing the gases, humidity is removed and the compound being measured (analyte) can be separated from potential interferents.

Preferably, in operation, the sensor will be used to identify a baseline spectrum for the patient prior to delivery, if necessary. This will prove beneficial for the detection of more than one drug if the patient receives more than one drug at a time and possible interference from different foods and odors in the stomach, mouth, esophagus and lungs.

Inhalational Anesthesia

Inhalation agents are generally administered through a breathing system. A breathing system is an assembly of components which connects the patient's airway to the anesthetic machine, from and into which the patient breathes. As known in the art, such systems generally include a fresh gas entry port/delivery tube through which the gases are delivered from the machine; a port to connect it to the patient's airway (oral airway, mask, endotracheal tube); a reservoir for gas; a expiratory port/valve through which the expired gas is vented to the atmosphere; a carbon dioxide absorber (for rebreathing); and tubes for connecting these components. Flow directing valves may or may not be used.

Figure 7A:
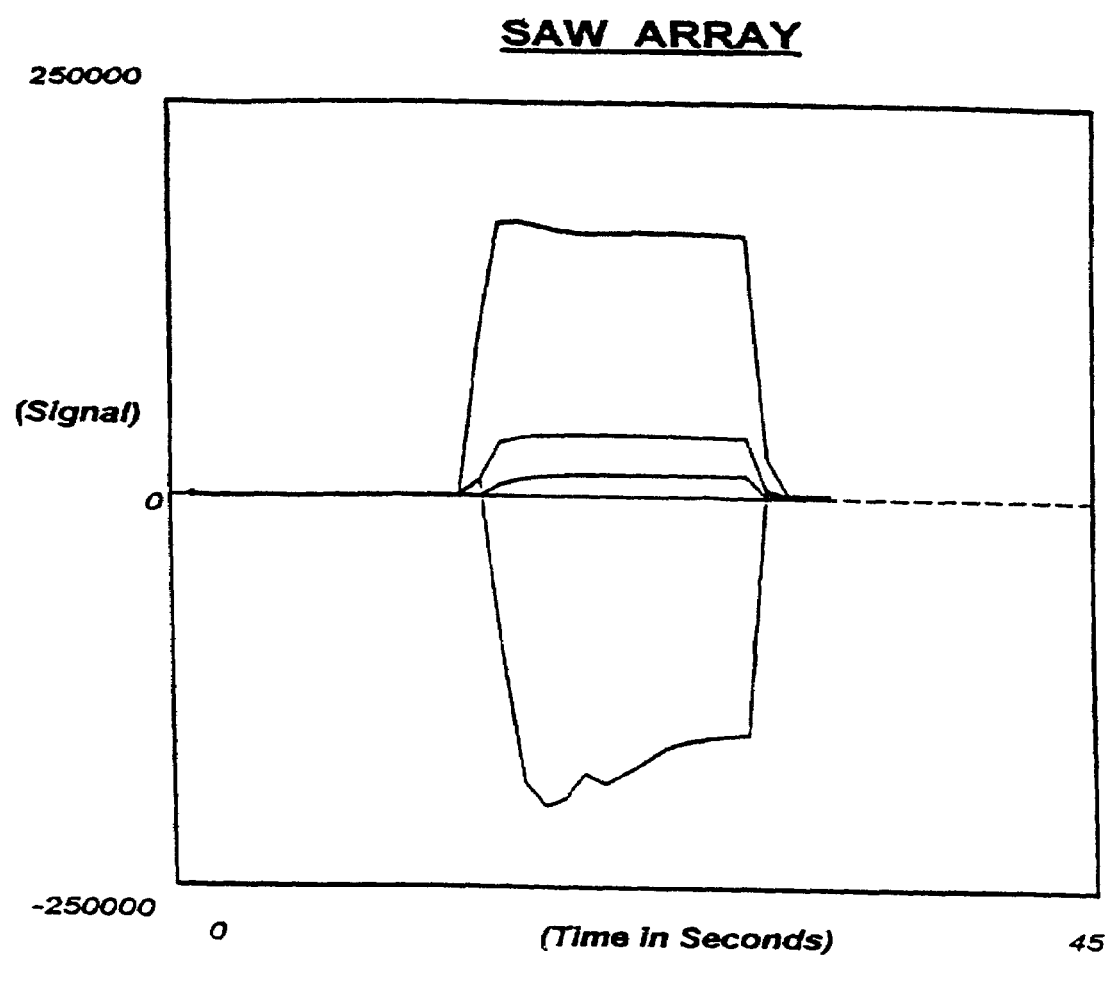
FIG. 7a shows the unique signature of Isoflurance derived from a SAW sensor.
Figure 7B:
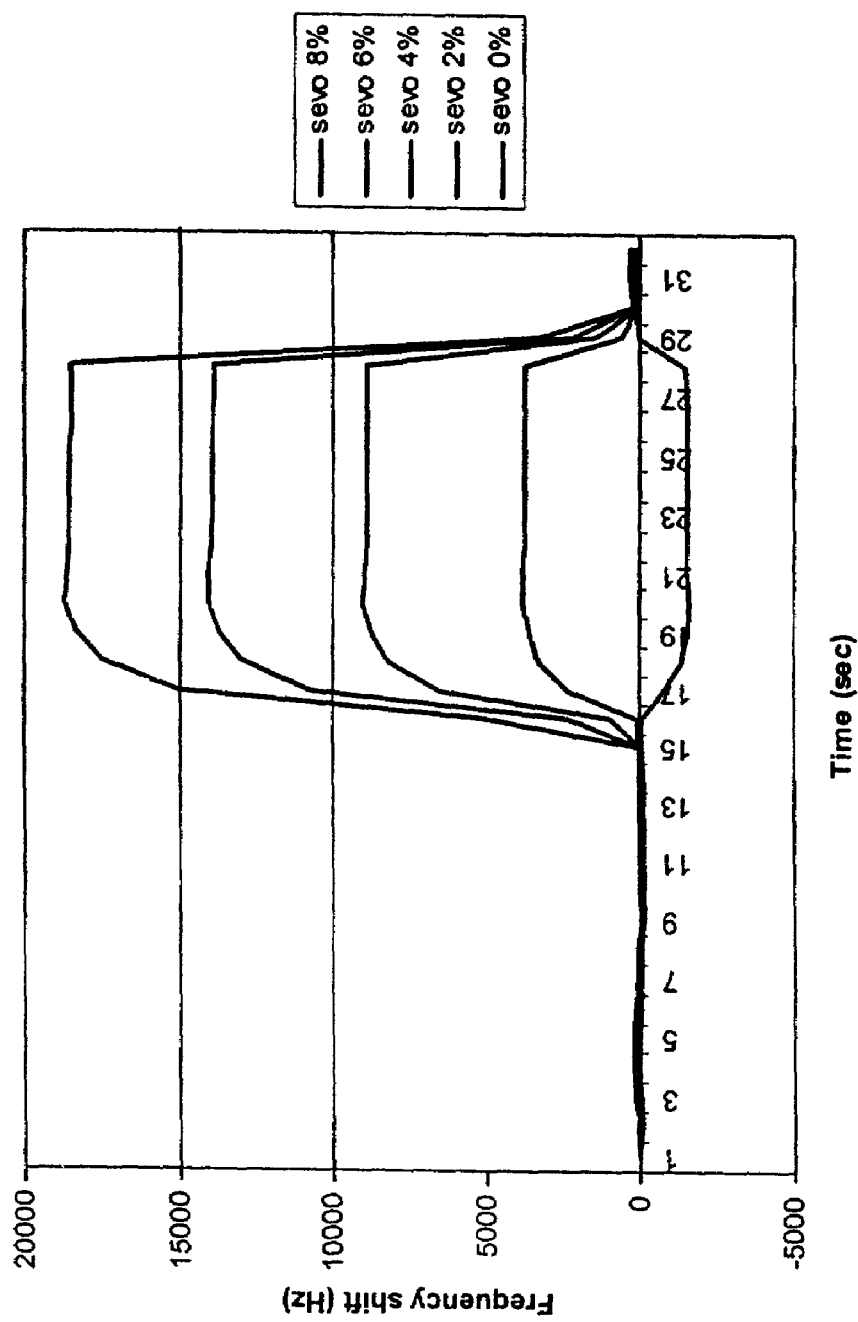
FIG. 7b shows the unique signature of Sevoflurane derived from a SAW sensor.

The sensors of the present invention are in communication with the delivered (inspired) gas and/or the expired gas of the breathing circuit to appropriately monitor the target substance(s). Preferably, the sensors are in flow communication with the appropriate tubes, valves, etc. of the circuit. FIGS. 7a and 7b show the unique signatures of the inhalational anesthetics Isoflurane and Sevoflurane, respectively, sampled from a breathing circuit. Sensors may be placed throughout the breathing circuit to obtain readings for target substances. Inspired gases are monitored by connecting the sensor(s) of the present invention to the appropriate location(s) in the breathing circuit. Similarly, expired gases are monitored by connecting the sensor(s) of the present invention to the appropriate location(s) in the breathing circuit. In an embodiment, samples are collected at the distal end of the endotracheal tube (ETT) through a tube with a separate sampling port. This may improve sampling by allowing a larger sample during each respiratory cycle. Monitored expired gases include, for example, physiologic gases and anesthetic gases. If IV anesthesia is also administered, as in "balanced anesthesia," monitoring expired gases will also include measuring concentration in the blood by the breath analysis of the present invention.

In an embodiment, side-stream monitoring is used. Moreover, a water trap, desiccant and/or filter may be used to remove water vapor and condensation from the sample. The device of the present invention continuously samples and measures inspired and exhaled (end-tidal) concentrations of respiratory gases. The monitored gases are both the physiologic gases found in the exhaled breath of patients (oxygen, carbon dioxide, and nitrogen), as well as those administered to the patient by the anesthesiologist in order to induce and maintain analgesia and anesthesia.

The sensors of the present invention may also monitor purity of gases at the entry port (fresh gas entry) and/or carrier gases. If multiple volatile anesthetic agents are connected to the circuit, an appropriate number of sensors may be included to detect each of such agents at the respective entry points as well as prior to inspiration.

Any number of sensors may be used at various points in the circuit to accomplish the desired monitoring. All of the sensors may connect to a single processor for analysis or use multiple processors. Similarly, the results of the monitoring may be displayed through a single display device or multiple display devices as desired. The method and apparatus of the present invention will detect and quantitate the concentration of the target substances.

Following are examples which illustrate procedures for practicing the invention. These examples should not be construed as limiting. All percentages are by weight and all solvent mixture proportions are by volume unless otherwise noted.

EXAMPLE I

Estimating the Depth of Intravenous Propofol Anesthesia by Measurement of Exhaled Breath Propofol Vapor Concentration and Monitoring Supplemental Inhalation Anesthesia The initial intravenous administration of propofol may be either in a bolus of 2 to 5 mg/kg or by a continuous infusion of 25 to 200 mcg/kg/min resulting in a plasma concentration in the 1 to 10 mcg/ml range. The depth of anesthesia (or sedation) achieved depends on patient characteristics as well as the simultaneous use of other drugs such as opioids and nitrous oxide.

For most administrations of propofol at anesthetic depth, the patient's ventilation occurs through a breathing circuit attached to the patient by an external face mask, a laryngeal mask airway (LMA), or by a tube placed in the trachea. These examples of a closed circuit all facilitate positive pressure ventilation if needed, the administration of supplemental inhalation anesthesia with nitrous oxide (also measured by sensors of the present invention), and the monitoring of ventilatory adequacy by carbon dioxide measurement. In addition the closed breathing circuit permits side-stream sampling of exhaled breath which can be diverted to the propofol measurement sensor. For non-closed circuit propofol sedation administration, a sampling catheter at the nares or mouth may be used to sample propofol vapor. A simultaneous carbon dioxide measurement may assist in the interpretation of the adequacy of the sampling.

The end-tidal portion of the exhaled breath is that fraction which has equilibrated with the blood returning from the systemic circulation to the lung. For the measurement methods cited below which allow multiple propofol vapor determinations per patient breath, the highest concentrations will be considered end-tidal propofol vapor concentrations. For slower analytical methods, the average exhaled concentrations will be used and corrected using end-tidal-to-average carbon dioxide concentration data. Alternatively, sampling line pressures or carbon dioxide levels may be used to instantaneously define end-tidal gas and direct only this portion of the sample stream to the sensor.

Within the clinical range, the blood level of propofol is directly related to the depth of propofol anesthesia. The blood to end-tidal gradient of propofol is theoretically dependent on four features 1) the vascular-to-alveolar propofol vapor transfer, 2) the matching of pulmonary ventilation to perfusion, 3) the delivery of a mixed alveolar gas sample to the sampling site, and 4) instrumentation accuracy and precision. The vascular-to-alveolar transfer is expected to be stable and predictable due to the small quantities of propofol involved and its highly polar nature. Ventilation-perfusion mismatch should impact propofol measurements less than carbon dioxide measurements due to the comparatively slow time course of propofol blood level changes. Likewise, adequate mixing of the respiratory gas sample by the time it reaches the sampling site should not be a problem compared to carbon dioxide sampling. A calibrated pressurized gas canister of propofol vapor will facilitate automatic recalibration as often as required to maintain sensor accuracy. Due to the relatively slow change of propofol blood levels in clinical work, multiple determinations may be used to improve precision.

The interpretation of the measured end-tidal propofol vapor concentration should emphasize two features: 1) the concentration itself relative to that likely to be required for the clinical scenario, and 2) trending of the propofol vapor concentration over time. The first feature, the magnitude of the concentration itself, may initially reflect incorrect dosing, extremes of age, altered protein binding, or other individual pharmacokinetic deviations. While a range of target propofol vapor concentrations may be expected, individual adjustment of a target level for the clinical scenario is required. Stimulating procedures such as endotracheal intubation, surgical incision, or movement of a fractured limb require a higher range than quiet sedation, anesthesia in a neurologically damaged patient, or anesthesia for a debilitated geriatric patient. The presence of opioids or other anesthetic agents such as nitrous oxide will also lower the target range of propofol vapor concentrations.

The second major feature of the interpretation of end-tidal propofol vapor concentration is trending of the concentration over time. When satisfactory anesthesia is initially established and a propofol infusion is started, an excessive rate of propofol may be inadvertently administered and the blood level may increase well beyond what is necessary and prudent. If the clinical scenario permits a trial reduction of the infusion rate until the patient becomes reactive then an excessive administration rate is ruled out. However, the danger of intraoperative movement in some cases, the simultaneous administration of paralytic agents, or the risk of intraoperative recall may prevent a trial reduction of what may appear to be an appropriate infusion rate. If one could be confident that accumulation of excess propofol in the blood was not occurring at a given rate of infusion as the administration progressed, trial infusion reductions would not be needed. Similarly, if the clearance of propofol in a given patient exceeded the infusion rate, sudden movement or wakefulness could be anticipated and avoided by increasing the infusion rate to maintain the current measured propofol level.

EXAMPLE II

Estimating the Blood Concentration of Supplemental Drugs Administered During Anesthesia and Their Concentration Trends by Measurement in Exhaled Breath. The Opioids Remifentanil and Alfentanil are Discussed as Examples The intravenous administration of remifentanil may be either in a bolus of 0.05 to 1 mcg/kg or by a continuous infusion of 0.0125 to 2 mcg/kg/min resulting in a plasma concentration in the 0.5 to 50 ng/ml range. Similarly, alfentanil, a related opioid, may be administered either in a bolus of 10 to 300 mcg/kg or by a continuous infusion of 0.1 to 15 mcg/kg/min resulting in a plasma concentration in the 10 to 500 ng/ml range. For both drugs the effect achieved depends on the dosage, individual patient characteristics, and the simultaneous administration of other drugs. The wide dosage ranges are a result of a wide range of desired effects; from analgesia during conscious sedation to deep general anesthesia when given to supplement a small dose of a hypnotic agent.

When remifentanil or alfentanil are administered during unconscious sedation or general anesthesia, the patient's ventilation occurs through a breathing circuit attached to the patient by an external face mask, a laryngeal mask airway (LMA), or by a tube placed in the trachea. These examples of a closed circuit all facilitate positive pressure ventilation due to the respiratory depressive effects of opioids, the administration of inhalation anesthetics and oxygen (also monitored by the present invention), and the monitoring of ventilatory adequacy by carbon dioxide measurement. In addition the closed breathing circuit permits side-stream sampling of exhaled breath which can be diverted to the remifentanil or alfentanil measurement sensor. For non-closed circuit remifentanil or alfentanil analgesia administration (usually during conscious sedation), a sampling catheter at the nares or mouth may be used to sample exhaled vapor. A simultaneous carbon dioxide measurement may assist in the interpretation of the adequacy of the sampling.

The end-tidal portion of the exhaled breath is that fraction which has equilibrated with the blood returning from the systemic circulation to the lung. For the measurement methods cited below which allow multiple remifentanil or alfentanil vapor determinations per patient breath, the highest concentrations will be considered end-tidal vapor concentrations. For slower analytical methods, the average exhaled concentrations will be used and corrected using end-tidal-to-average carbon dioxide concentration data. Alternatively, sampling line pressures or carbon dioxide concentrations may be used to instantaneously define end-tidal gas and direct only this portion of the sample stream to the sensor.

Within the clinical range, the blood concentration of the opioids remifentanil and alfentanil are directly related to their pharmacodynamic effects. The blood to end-tidal gradient of remifentanil and alfentanil is theoretically dependent on four features 1) the vascular-to-alveolar transfer of the drug, 2) the matching of pulmonary ventilation to perfusion, 3) the delivery of a mixed alveolar gas sample to the sampling site, and 4) instrumentation accuracy and precision. The vascular-to-alveolar transfer is expected to be stable and predictable due to the small quantities of remifentanil or alfentanil involved and its highly polar nature. Ventilation-perfusion mismatch should impact measurements less than carbon dioxide measurements due to the comparatively slow time course of remifentanil and alfentanil blood concentration changes. Likewise, adequate mixing of the respiratory gas sample by the time it reaches the sampling site should not be a problem compared to carbon dioxide sampling. A calibrated pressurized gas canister of the drug vapor will facilitate automatic recalibration as often as required to maintain sensor accuracy. Due to the relatively slow change of blood concentration of these opioids in clinical work, multiple determinations may be used to improve precision.

The interpretation of the measured end-tidal opioid vapor concentration should emphasize two features: 1) the concentration itself relative to that likely to be required for the clinical scenario (in the nanograms per mL of plasma range), and 2) trending of the opioid vapor concentration over time. The first feature, the magnitude of the concentration itself, may initially reflect incorrect dosing, extremes of age, altered protein binding, or other individual pharmacokinetic deviations. While a range of target opioid vapor concentrations may be expected, individual adjustment of a target concentration for the clinical scenario is required. Pharmacologic tolerance and the widely ranging intensity of painful surgical stimuli will alter concentration requirements greatly. The presence of other anesthetic agents such as inhalation anesthetics or regional anesthesia will lower the target range of opioid vapor concentrations.

The second major feature of the interpretation of end-tidal opioid vapor concentration is trending of the concentration over time. After a satisfactory opioid effect is initially established with bolus injections of the remifentanil or alfentanil and a remifentanil or alfentanil infusion is subsequently started, an excessive rate of infusion or drug interactions or low drug metabolism may occur and the blood concentrations may increase well beyond what is necessary and prudent. If the clinical scenario permits a trial reduction of the infusion rate until the patients condition indicates inadequate dosing then an excessive administration rate is ruled out. However, the danger of intraoperative movement in some cases, the simultaneous administration of paralytic agents, or the risk of light anesthesia with intraoperative recall may prevent a trial reduction from what may appear to be an appropriate infusion rate. If one could be confident that accumulation of excess opioids in the blood as reflected in the exhaled breath measurement was not occurring as the administration progressed at a given rate of infusion, trial infusion reductions would not be needed. Similarly, if the clearance of remifentanil or alfentanil in a given patient exceeded the infusion rate, sudden movement or signs of inadequate anesthesia could be anticipated and avoided by increasing the infusion rate to maintain the current measured opioid vapor concentration.

In addition to the rapidly acting opioids remifentanil and alfentanil discussed above, similar exhaled vapor assessment of fentanyl and sufentanil may be clinically useful as an indirect indicator of blood concentrations. Other non-opioid intravenous anesthetics and anesthetic adjuncts such as etomidate, ketamine, and barbiturates (particularly those of short-duration) may also be administered more precisely and safely with monitoring of their exhaled vapor concentrations as a non-invasive rapid estimate of their blood concentration.

EXAMPLE III

Measuring Endogenous and Exogenous Compounds such as, Ketones and Ammonia in Exhaled Breath Normally, the exhaled breath of a person contains water vapor, carbon dioxide, oxygen, and nitrogen, and trace concentrations of carbon monoxide, hydrogen and argon, all of which are odorless. A common medical problem is halitosis, which is usually caused by the breakdown of food by bacteria producing odorants such as hydrogen sulfide, methyl mercaptan, dimethyl disulphide, indole and others. The sensor technology described herein may be used as a sensitive detector for these odorants and for the diagnosis of tooth decay, gum disease or a variety of oral, pulmonary and sinus conditions.

Other vapor phase compounds include acetone, which is present in diabetics who are in ketoacidosis, ammonia, which is present in patients with liver disease and a variety of odorants which are present in cases of lungs, stomach, gallbladder and kidney dysfunction. Exhaled breath sensing of these compounds may be a highly sensitive method of diagnosing and following the course of treatment of these diseases. The potential for evaluating exhaled breath for markers of carcinoma is being actively explored, and the sensor technology may play a role in this area as well.

One particularly valuable non-invasive test that is based on exhaled breath detection, is the test for Helicobacter pylori, the bacterium responsible for stomach ulcers. Subjects are given a 75 mg dose of urea tagged with carbon isotopes to drink and the exhaled breath is evaluated for tagged carbon dioxide. Helicobacter pylori secretes the enzyme urease to protect the organism from the acidity of the stomach. The urease breaks down the tagged urea to ammonia and carbon dioxide. While conventional tests measure the tagged carbon dioxide, they are time consuming and expensive. The sensor technology could be used to measure ammonia in the breath quickly and cheaply and alleviate the need to use a radiolabel compound.

Other non-invasive tests for the detection of other pathologic organisms is the gastrointestinal tract and in body fluids can be developed that take advantage of the sensor technology.

EXAMPLE IV

Selection of Sensors

The following are examples of various sensor technologies that may be utilized in practicing the method of the present invention:

Conducting Polymers

Conducting polymer sensors promise fast response time, low cost, and good sensitivity and selectivity. The technology is relatively simple in concept. A conductive material, such as carbon, is homogeneously blended in a specific non-conducting polymer and deposited as a thin film on an aluminum oxide substrate. The films lie across two electrical leads, creating a chemoresistor. As the polymer is subjected to various chemical vapors, it expands, increasing the distance between carbon particles, and thereby increasing the resistance. The polymer matrix swells because analyte vapor absorbs into the film to an extent determined by the partition coefficient of the analyte. The partition coefficient defines the equilibrium distribution of an analyte between the vapor phase and the condensed phase at a specified temperature. Each individual detector element requires a minimum absorbed amount of analyte to cause a response noticeable above the baseline noise. Selectivity to different vapors is accomplished by changing the chemical composition of the polymer. This allows each sensor to be tailored to specific chemical vapors. Therefore, for most applications an array of orthogonal responding sensors is required to improve selectivity. Regardless of the number of sensors in the array, the information from them must be processed with pattern recognition software to correctly identify the chemical vapors of interest. Sensitivity concentration are reportedly good (tens of ppm). The technology is very portable (small and low power consumption), relatively fast in response time (less than 1 minute), low cost, and should be rugged and reliable Electrochemical Sensors Electrochemical sensors rely on an irreversible chemical reaction to measure. They contain an electrolyte that reacts with a specific gas, producing an output signal that is proportional to the amount of gas present. Electrochemical sensors exist for gases such as chlorine, carbon monoxide, hydrogen sulfide, and hydrogen, but cannot be used to measure hydrocarbons. The number of gases that can be detected using this technology is relatively small, but is increasing from year to year.

Electrochemical sensors are excellent for detecting low parts-per-million concentrations. They are also rugged, draw little power, linear and do not require significant support electronics or vapor handling (pumps, valves, etc.) They are moderate in cost ($50 to $200 in low volumes) and small in size.

Gas Chromatography/Mass Spectroscopy (GC/MS)

Gas Chromatography/Mass Spectroscopy (GC/MS) is actually a combination of two technologies. One technology separates the chemical components (GC) while the other one detects them (MS). Technically, gas chromatography is the physical separation of two or more compounds based on their differential distribution between two phases, the mobile phase and stationary phase. The mobile phase is a carrier gas that moves a vaporized sample through a column coated with a stationary phase where separation takes place. When a separated sample component elutes from the column, a detector converts the column eluent to an electrical signal that is measured and recorded. The signal is recorded as a peak in the chromatogram plot. Chromatograph peaks can be identified from their corresponding retention times. The retention time is measured from the time of sample injection to the time of the peak maximum, and is unaffected by the presence of other sample components. Retention times can range from seconds to hours, depending on the column selected and the component. The height of the peak relates to the concentration of a component in the sample mixture.

After separation, the chemical components need to be detected. Mass spectroscopy is one such detection method, which bombards the separated sample component molecules with an electron beam as they elute from the column. This causes the molecules to lose an electron and form ions with a positive charge. Some of the bonds holding the molecule together are broken in the process, and the resulting fragments may rearrange or break up further to form more stable fragments. A given compound will ionize, fragment, and rearrange reproducibly under a given set of conditions. This makes identification of the molecules possible. A mass spectrum is a plot showing the mass/charge ratio versus abundance data for ions from the sample molecule and its fragments. This ratio is normally equal to the mass for that fragment. The largest peak in the spectrum is the base peak. The GC/MS is accurate, selective and sensitive.

Infrared Spectroscopy (FTIR, NDIR)

Infrared (IR) spectroscopy is one of the most common spectroscopic techniques used by organic and inorganic chemists. Simply, it is the absorption measurement of different IR frequencies by a sample positioned in the path of an IR beam. IR radiation spans a wide section of the electromagnetic spectrum having wavelengths from 0.78 to 1000 micrometers (microns). Generally, IR absorption is represented by its wave number, which is the inverse of its wavelength times 10,000. For a given sample to be detected using IR spectroscopy, the sample molecule must be active in the IR region, meaning that the molecule must vibrate when exposed to IR radiation. Several reference books are available which contain this data, including the Handbook of Chemistry and Physics from the CRC Press.

There are two general classes of IR spectrometers—dispersive and non-dispersive. In a typical dispersive IR spectrometer, radiation from a broadband source passes through the sample and is dispersed by a monochromator into component frequencies. The beams then fall on a detector, typically a thermal or photon detector, which generates an electrical signal for analysis. Fourier Transform IR spectrometers (FTIR) have replaced the dispersive IR spectrometer due to their superior speed and sensitivity. FTIR eliminates the physical separation of optical component frequencies by using a moving mirror Michelson interferometer and taking the Fourier transform of the signal.

Conversely, in the non-dispersive IR (NDIR) spectrometer, instead of sourcing a broad IR spectrum for analyzing a range of sample gases, the NDIR sources a specific wavelength which corresponds to the absorption wavelength of the target sample. This is accomplished by utilizing a relatively broad IR source and using spectral filters to restrict the emission to the wavelength of interest. For example, NDIR is frequently used to measure carbon monoxide (CO), which absorbs IR energy at a wavelength of 4.67 microns. By carefully tuning the IR source and detector during design, a high volume production CO sensor is manufactured. This is particularly impressive, as carbon dioxide is a common interferent and has an IR absorption wavelength of 4.26 microns, which is very close to that of CO.

NDIR sensors promise low cost (less than $200), no recurring costs, good sensitivity and selectivity, no calibration and high reliability. They are small, draw little power and respond quickly (less than 1 minute). Warm up time is nominal (less than 5 minutes). Unfortunately, they only detect one target gas. To detect more gases additional spectral filters and detectors are required, as well as additional optics to direct the broadband IR source.

Ion Mobility Spectrometry (IMS)

Ion Mobility Spectrometry (IMS) separates ionized molecular samples on the basis of their transition times when subjected to an electric field in a tube. As the sample is drawn into the instrument, it is ionized by a weak radioactive source. The ionized molecules drift through the cell under the influence of an electric field. An electronic shutter grid allows periodic introduction of the ions into the drift tube where they separate based on charge, mass, and shape. Smaller ions move faster than larger ions through the drift tube and arrive at the detector sooner. The amplified current from the detector is measured as a function of time and a spectrum is generated. A microprocessor evaluates the spectrum for the target compound, and determines the concentration based on the peak height.

IMS is an extremely fast method and allows near real time analysis. It is also very sensitive, and should be able to measure all the analytes of interest. IMS is moderate in cost (several thousand dollars) and larger in size and power consumption.

Metal Oxide Semiconductor (MOS) Sensors

Metal Oxide Semiconductor (MOS) sensors utilize a semiconducting metal-oxide crystal, typically tin-oxide, as the sensing material. The metal-oxide crystal is heated to approximately 400° C., at which point the surface adsorbs oxygen. Donor electrons in the crystal transfer to the adsorbed oxygen, leaving a positive charge in the space charge region. Thus, a surface potential is formed, which increases the sensor's resistance. Exposing the sensor to deoxidizing, or reducing, gases removes the surface potential, which lowers the resistance. The end result is a sensor which changes its electrical resistance with exposure to deoxidizing gases. The change in resistance is approximately logarithmic.

MOS sensors have the advantage of being extremely low cost (less than $8 in low volume) with a fast analysis time (milliseconds to seconds). They have long operating lifetimes (greater than five years) with no reported shelf life issues.

Photo-Ionization Detectors (PID)

Photo-Ionization Detectors rely on the fact that all elements and chemicals can be ionized. The energy required to displace an electron and 'ionize' a gas is called its Ionization Potential (IP), measured in electron volts (eV). A PID uses an ultraviolet (UV) light source to ionize the gas. The energy of the UV light source must be at least as great as the IP of the sample gas. For example, benzene has an IP of 9.24 eV, while carbon monoxide has an IP of 14.01 eV. For the PID to detect the benzene, the UV lamp must have at least 9.24 eV of energy. If the lamp has an energy of 15 eV, both the benzene and the carbon monoxide would be ionized. Once ionized, the detector measures the charge and converts the signal information into a displayed concentration. Unfortunately, the display does not differentiate between the two gases, and simply reads the total concentration of both summed together.

Three UV lamp energies are commonly available: 9.8, 10.6 and 11.7 eV. Some selectivity can be achieved by selecting the lowest energy lamp while still having enough energy to ionize the gases of interest. The largest group of compounds measured by a PID are the organics (compounds containing carbon), and they can typically be measured to parts per million (ppm) concentrations. PIDs do not measure any gases with an IP greater than 11.7 eV, such as nitrogen, oxygen, carbon dioxide and water vapor. The CRC Press Handbook of Chemistry and Physics includes a table listing the IPs for various gases.

PIDs are sensitive (low ppm), low cost, fast responding, portable detectors. They also consume little power.

Surface Acoustic Wave Sensors (SAW)

Surface Acoustic Wave (SAW) sensors are constructed with interdigitated metal electrodes fabricated on piezoelectric substrates both to generate and to detect surface acoustic waves. Surface acoustic waves are waves that have their maximum amplitude at the surface and whose energy is nearly all contained within 15 to 20 wavelengths of the surface. Because the amplitude is a maximum at the surface such devices are very surface sensitive. Normally, SAW devices are used as electronic bandpass filters in cell phones. They are hermetically packaged to insure that their performance will not change due to a substance contacting the surface of the SAW die.

SAW chemical sensors take advantage of this surface sensitivity to function as sensors. To increase specificity for specific compounds, SAW devices are frequently coated with a thin polymer film that will affect the frequency and insertion loss of the device in a predictable and reproducible manner. Each sensor in a sensor array is coated with a different polymer and the number and type of polymer coating are selected based on the chemical to be detected. If the device with the polymer coating is then subjected to chemical vapors that absorb into the polymer material, then the frequency and insertion loss of the device will further change. It is this final change that allows the device to function as a chemical sensor.

If several SAW devices are each coated with a different polymer material, the response to a given chemical vapor will vary from device to device. The polymer films are normally chosen so that each will have a different chemical affinity for a variety of organic chemical classes, that is, hydrocarbon, alcohol, ketone, oxygenated, chlorinated, and nitrogenated. If the polymer films are properly chosen, each chemical vapor of interest will have a unique overall effect on the set of devices. SAW chemical sensors are useful in the range of organic compounds from hexane on the light, volatile extreme to semi-volatile compounds on the heavy, low volatility extreme.

Motors, pumps and valves are used to bring the sample into and through the array. The sensitivity of the system can be enhanced for low vapor concentrations by having the option of using a chemical preconcentrator before the array. In operation, the preconcentrator absorbs the test vapors for a period of time and is then heated to release the vapors over a much shorter time span thereby increasing the effective concentration of the vapor at the array. The system uses some type of drive and detection electronics for the array. An on board microprocessor is used to control the sequences of the system and provide the computational power to interpret and analyze data from the array.

SAW sensors are reasonably priced (less than $200) and have good sensitivity (tens of ppm) with very good selectivity. They are portable, robust and consume nominal power. They warm up in less than two minutes and require less than one minute for most analysis. They are typically not used in high accuracy quantitative applications, and thus require no calibration. SAW sensors do not drift over time, have a long operating life (greater than five years) and have no known shelf life issues. They are sensitive to moisture, but this is addressed with the use of a thermally desorbed concentrator and processing algorithms.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of monitoring a patient during administration of anesthesia wherein said patient is connected to a breathing circuit, comprising:
    exposing at least one sensor to inspired and expired gases; and
    detecting one or more target substances with said sensor, wherein at least one anesthetic agent is delivered intravenously, and wherein the one or more target substances are indicative of the at least one anesthetic agent.

2. The method of claim 1 wherein said target substance is an anesthetic agent.

3. The method of claim 1 wherein said target substance is a physiologic gas.

4. The method of claim 1 wherein said target substance is a gas supplied to a breathing circuit.

5. The method of claim 1 further comprising:
    determining the depth of anesthesia based on the concentration of at least one target substance detected in said expired gases.

6. The method of claim 5 further comprising
    controlling an infusion pump for delivering said at least one agent intravenously based on the depth of anesthesia determined.

7. The method of claim 5 wherein the concentration is measured to determine anesthetic blood concentration.

8. The method of claim 5 wherein the concentration is measured to determine analgesic blood concentration.

9. The method of claim 1 wherein separate sensors are exposed to inspired and expired gases.

10. The method of claim 1 wherein one or more target substances are detected after a predetermined period of time.

11. The method of claim 1 further comprising the step of using at least one flow sensor to detect flow of gases.

12. The method of claim 1 wherein the detecting step comprises detecting both presence and concentration of the target substance.

13. The method of claim 12 wherein the concentration is indicative of a rate of metabolism of the target substance.

14. The method of claim 1 wherein the steps are repeated periodically to monitor trending over time.

15. The method of claim 1 wherein the agent is for sedation.

16. The method of claim 1 wherein a combination of agents is administered.

17. The method of claim 1 wherein the detecting is continuous.

18. The method of claim 1 wherein the detecting is periodic.

19. The method of claim 1 further comprising the step of recording data from said sensor.

20. The method of claim 1 further comprising the step of transmitting data from said sensor.

21. The method of claim 1 further comprising comparing the substance detected with a predetermined signature profile.

22. The method of claim 1 further comprising
    capturing a sample of expired gases prior to exposing said sensor to expired gases.

23. The method of claim 1 further comprising
    dehumidifying expired gases prior to exposing said sensor to expired gases.

24. The method of claim 1 further comprising
    detecting exhalation of the patient's breath with a sensor.

25. The method of claim 1 wherein said target substance is an unbound anesthetic agent indicative of the anesthetic agent.

26. A method of monitoring a patient during administration of anesthesia wherein said patient is connected to a breathing circuit, comprising:
    exposing at least one sensor to inspired and expired gases; and
    detecting one or more target substances with said sensor, wherein at least one anesthetic agent is administered through said breathing circuit, and wherein at least one additional anesthetic agent is delivered intravenously.

27. A method of monitoring a patient during intravenous administration of anesthesia wherein said patient is connected to a breathing circuit, comprising:
    exposing at least one sensor to inspired and expired gases;
    detecting one or more target substances with said sensor; and
    determining the depth of amnesia based on the concentration of at least one target substance detected in said expired gases, wherein the target substance is for amnesia.

28. A method of monitoring a patient during intravenous administration of anesthesia wherein said patient is connected to a breathing circuit, comprising:
    exposing at least one sensor to inspired and expired gases;
    detecting one or more target substances with said sensor; and
    determining the depth of analgesia based on the concentration of at least one target substance detected in said expired gases, wherein the target substance is for analgesia.

29. A method of monitoring a patient during intravenous administration of anesthesia wherein said patient is connected to a breathing circuit, comprising:
    exposing at least one sensor to inspired and expired gases;
    detecting one or more target substances with said sensor; and
    determining the depth of muscle relaxation based on the concentration of at least one target substance detected in said expired gases, wherein the target substance is for muscle relaxation.

30. A method of monitoring a patient during administration of anesthesia wherein said patient is connected to a breathing circuit, comprising:
    exposing at least one sensor to inspired and expired gases; and detecting one or more target substances with said sensor, wherein said target substance is an unbound anesthetic agent and a metabolite of an anesthetic agent indicative of the anesthetic agent.

31. A method of monitoring a patient during administration of anesthesia wherein said patient is connected to a breathing circuit, comprising:
   exposing at least one sensor to inspired and expired gases;
   detecting one or more target substances with said sensor; and
   assigning a numerical value to the concentration as analyzed upon reaching a level of anesthetic effect in said patient and, thereafter, assigning higher or lower values to the concentration based on its relative changes,
wherein the detecting step comprises detecting both presence and concentration of the target substance, and wherein at least one anesthetic agent is delivered intravenously.

32. A method of monitoring a patient during administration of anesthesia wherein said patient is connected to a breathing circuit, comprising:
   exposing at least one sensor to inspired and expired gases;
   detecting one or more target substances with said sensor;
   assigning a numerical value to the concentration as analyzed upon reaching a level of anesthetic effect in said patient and, thereafter, assigning higher or lower values to the concentration based on its relative changes; and
   monitoring the concentration by monitoring changes in said value and adjusting administration of anesthesia to maintain a desired anesthetic effect,
wherein the detecting step comprises detecting both presence and concentration of the target substance, and wherein at least one anesthetic agent is delivered intravenously.

33. A method of monitoring a patient during administration of anesthesia wherein said patient is connected to a breathing circuit, comprising:
   exposing a first sensor to inspired gases, wherein at least one inspired gas is an anesthetic agent;
   exposing a second sensor to expired gases;
   detecting one or more target substances with said first and second sensors; and
   determining concentration of said target substances;
wherein the first and second sensors are different sensors.

34. A method of monitoring a patient during administration of anesthesia wherein said patient is connected to a breathing circuit, comprising:
   exposing at least one sensor to inspired and expired gases; and
   detecting one or more target substances with said sensor,
wherein at least one anesthetic agent is delivered intravenously and wherein said target substance is an anesthetic agent.

35. A method of monitoring a patient during administration of anesthesia wherein said patient is connected to a breathing circuit, comprising:
   exposing at least one sensor to inspired and expired gases; and
   detecting one or more target substances with said sensor,
wherein at least one anesthetic agent is delivered intravenously and wherein said target substance is a physiologic gas.

36. A method of monitoring a patient during administration of anesthesia wherein said patient is connected to a breathing circuit, comprising:
   exposing at least one sensor to inspired and expired gases; and
   detecting one or more target substances with said sensor,
wherein at least one anesthetic agent is delivered intravenously and wherein said target substance is a gas supplied to a breathing circuit.

* * * * *

UNITED STATES PATENT AND TRADEMARK OFFICE
CERTIFICATE OF CORRECTION

| | |
|---|---|
| PATENT NO. | : 6,981,947 B2 |
| APPLICATION NO. | : 10/178877 |
| DATED | : January 3, 2006 |
| INVENTOR(S) | : Richard J. Melker, David G. Bjoraker and Samsun Lampotang |

Page 1 of 1

It is certified that error appears in the above-identified patent and that said Letters Patent is hereby corrected as shown below:

Cover Page,
"(75) Inventor: Richard J. Melker, Gainesville, FL (US)" should read --(75) Inventors: Richard J. Melker, Gainesville, FL (US); David G. Bjoraker, Gainesville, FL (US); Samsun Lampotang, Gainesville, FL (US)--.

Column 25,
Line 62, Claim 15, "agent" should read --target substance--.

Signed and Sealed this

Fourteenth Day of August, 2007

JON W. DUDAS
*Director of the United States Patent and Trademark Office*